US012590103B2

(12) United States Patent
Zhang et al.

(10) Patent No.: US 12,590,103 B2
(45) Date of Patent: Mar. 31, 2026

(54) POLYMORPH OF EP4 RECEPTOR ANTAGONIST, PREPARATION METHOD THEREFOR AND USE THEREOF

(71) Applicant: SHANGHAI YUYAO BIOTECH LTD., Shanghai (CN)

(72) Inventors: Hankun Zhang, Shanghai (CN); Junjie Yang, Shanghai (CN); Mingyao Liu, Shanghai (CN); Wenbo Zhou, Shanghai (CN); Shihong Peng, Shanghai (CN); Huang Chen, Shanghai (CN); Jian Lu, Shanghai (CN)

(73) Assignee: SHANGHAI YUYAO BIOTECH LTD., Shanghai (CN)

( * ) Notice: Subject to any disclaimer, the term of this patent is extended or adjusted under 35 U.S.C. 154(b) by 823 days.

(21) Appl. No.: 17/797,804

(22) PCT Filed: Jan. 29, 2021

(86) PCT No.: PCT/CN2021/074485

§ 371 (c)(1),
(2) Date: Aug. 5, 2022

(87) PCT Pub. No.: WO2021/155766

PCT Pub. Date: Aug. 12, 2021

(65) Prior Publication Data

US 2023/0074179 A1 Mar. 9, 2023

(30) Foreign Application Priority Data

Feb. 5, 2020 (CN) ......................... 202010080620.6

(51) Int. Cl.

| | |
|---|---|
| ***C07D 495/04*** | (2006.01) |
| ***A61P 19/00*** | (2006.01) |
| ***A61P 29/00*** | (2006.01) |
| ***A61P 35/00*** | (2006.01) |
| ***A61P 37/00*** | (2006.01) |

(52) U.S. Cl.

CPC ............ *C07D 495/04* (2013.01); *A61P 19/00* (2018.01); *A61P 29/00* (2018.01); *A61P 35/00* (2018.01); *A61P 37/00* (2018.01); *C07B 2200/13* (2013.01)

(58) Field of Classification Search

CPC ... C07D 495/04; C07B 2200/13; A61P 35/00; A61P 37/00; A61P 19/00

See application file for complete search history.

(56) References Cited

U.S. PATENT DOCUMENTS 8,598,355 B2 12/2013 Nozawa et al.

FOREIGN PATENT DOCUMENTS

| | | | | |
|---|---|---|---|---|
| CN | 109836434 A | 6/2019 | | |
| CN | 110386941 A | 10/2019 | | |
| WO | 2009139373 A1 | 11/2009 | | |
| WO | WO-2019101171 A1 | * | 5/2019 | ........... A61K 31/381 |
| WO | 2019166022 A1 | 9/2019 | | |
| WO | 2021155766 A1 | 8/2021 | | |
| WO | 2022138793 A1 | 6/2022 | | |

OTHER PUBLICATIONS

The Chemical Society of Japan, Chemistry Handbook Applied Chemistry Edition 6th Edition; Chapter 4; Jan. 30, 2003; pp. 178; ISBN462107138-6.

Shioji, Yuusaku; "Manufacturing technology for solid dosage forms(Non-official translation)"; CMC Publishing co., Ltd; Jan. 27, 2003; pp. 9, 12-13; ISBN4-88231-783-4.

Asahara, Teruzo et al.; "Solvent Handbook"; Kodansha; Year: 1985; pp. 47-51; ISBN4-06-129882-8(0).

Ashizawa, Y.; "Optimization and industrialization of salt and crystal forms(Non-official translation)"; Pharm Tech Japan; vol. 18, No. 10; Sep. 2002; pp. 81-96.

Hirayama, Noriaki; "Organic compound crystal preparation handbook(Non-official translation)"; Maruzen Publishing; Chapter 4; Jul. 25, 2008; pp. 57-84; ISBN978-4-621-07991-1.

Kojima, Takashi; "Aiming to improve the efficiency of crystal form selection in drug development(Non-official translation)"; Pharmacy; vol. 68, No. 5; Sep. 1, 2008; pp. 344-349.

Slaby, Maria; "First office Action for Application No. 3,167,083(PCT No. CN2021074485)"; Innovation, Science and Economic Development Canada; Sep. 19, 2023; pp. 1-5.

Caira, Mino R. "Crystalline Polymorphism of Organic Compounds"; Topics in Current chemistry, vol. 198; Jan. 1, 1998; ISSN: 0340-1022; pp. 163-208.

* cited by examiner

*Primary Examiner* — Brenda L Coleman
*Assistant Examiner* — Madeline E Braun
(74) *Attorney, Agent, or Firm* — NKL Law; Bin Lu; Allen Xue

(57) ABSTRACT

Provided are a polymorph of an EP4 receptor antagonist, a preparation method therefor and a use thereof, relating in particular to a polymorph of an EP4 receptor antagonist(S)-4-(1-(2-(4-fluorobenzyl)-4, 7-dihydro-5H-thieno [2,3-c] pyran-3-carboxamido) ethyl) benzoic acid, a preparation method therefor and a use thereof. Compared with an amorphous form of a compound represented by formula I, the polymorph of the present invention has higher stability and better processing performance and is very suitable for being prepared into a medicine.

12 Claims, 25 Drawing Sheets

POLYMORPH OF EP4 RECEPTOR ANTAGONIST, PREPARATION METHOD THEREFOR AND USE THEREOF

TECHNICAL FIELD

The invention relates to the field of pharmaceutical chemistry, in particular to a polymorph of an EP4 receptor antagonist (S)-4-(1-(2-(4-fluorobenzyl)-4,7-dihydro-5H-thieno [2,3-c]pyran-3-carboxamido) ethyl) benzoic acid, and preparation method therefor and use thereof.

BACKGROUND (S)-4-(1-(2-(4-fluorobenzyl)-4,7-dihydro-5H-thieno [2,3-c]pyran-3-carboxamido) ethyl) benzoic acid (compound of formula I) is a highly active and highly selective prostaglandin $E_2$ receptor EP4 antagonist. The EP4 receptor antagonist has no inhibitory activity on normal cells and tumor cells, but is useful in treating or alleviating EP4 receptor activity, especially in diseases and disorders mediated by EP4 receptor agonistic activity, and has more stable metabolism and good hydrophilicity, which basically meets the requirements for drug formation. Such diseases are as follows: liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, Lymphoma, cervical cancer and other malignant tumors, allergies, inflammation, bone diseases, acute or chronic pain. The structural formula is as follows:

I

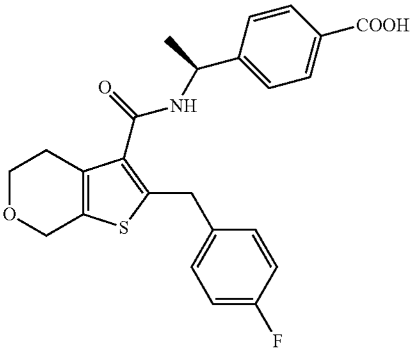

The preparation method of the compound is disclosed in the international application number PCT/CN2018/117235, but the crystalline form of the compound is not involved, and there is no other literature report the crystalline form of (S)-4-(1-(2-(4-fluorobenzyl)-4,7-dihydro-5H-thieno [2,3-c] pyran-3-carboxamido) ethyl) benzoic acid. The polymorphic form of the drug is of great significance to the physical and chemical properties, pharmacokinetic properties, formulation quality, in vivo and in vitro pharmacological properties and processes of the drug. The difference in physicochemical properties due to the different crystalline forms of the drug will affect the drug solubility, stability, drug release rate, safety, in vivo bioavailability and the exertion of good efficacy. The difference in surface free energy of different crystalline forms will affect the particle size, uniformity, distribution uniformity and physical stability of the drug.

Therefore, there is a need in the art to provide polymorphic form of the compound of Formula I that are more stable and more suitable for drug formation.

SUMMARY OF THE INVENTION

The purpose of the present invention is to provide polymorphic forms of (S)-4-(1-(2-(4-fluorobenzyl)-4,7-dihydro-5H-thieno [2,3-c] pyran-3-formamido) ethyl) benzoic acid, as well as the preparation method therefor and application thereof.

In the first aspect of the present invention, it provides polymorph of the compound of formula I, wherein the polymorph is selected from the group consisting of polymorphic Form I, polymorphic Form II, polymorphic Form III, polymorphic Form IV, polymorphic Form V, and polymorphic Form VI,

I

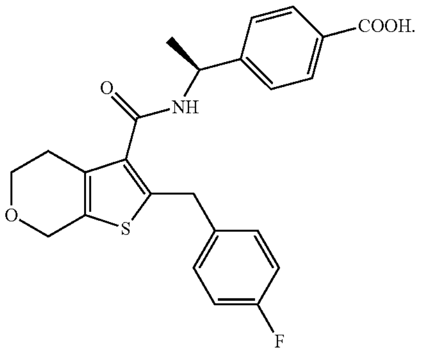

In another preferred embodiment, the X-ray powder diffraction pattern of the polymorphic Form I has characteristic peaks at 2θ values of 4.234±0.2°, 8.505±0.2°, 8.96±0.2°, 11.177±0.2°, 12.892±0.2°, 18.05±0.2°, 23.333±0.2°.

In another preferred embodiment, the X-ray powder diffraction pattern of the polymorphic Form I also has characteristic peaks at one or more 2θ values selected from the group consisting of 10.05±0.2°, 16.438±0.2°, 17.093±0.2°, 19.229±0.2°, 20.259±0.2°, 21.544±0.2°, 25.613±0.2°, 26.051±0.2°.

In another preferred embodiment, the X-ray powder diffraction pattern of the polymorphic Form I also has characteristic peaks at one or more 2θ values selected from the group consisting of 18.851±0.2°, 19.406±0.2°, 22±0.2°, 22.543±0.2°, 24.285±0.2°, 26.774±0.2°, 27.331±0.2°, 28.441±0.2°, 29.04±0.2°, 29.529±0.2°, 30.185±0.2°, 33.196±0.2°, 34.049±0.2°, 34.714±0.2°, 36.109±0.2°, 37.076±0.2°, 38.936±0.2°.

In another preferred embodiment, the polymorphic Form I has one or more features selected from the group consisting of:

a) the polymorphic Form I is anhydrous and solvent-free crystal form;

b) in the TGA pattern, the weight loss of the polymorphic Form I is about 0.1-1% from room temperature to 230° C., preferably 0.2-0.5%;

c) in the DSC pattern, the polymorphic Form I has an endothermic peak with a shoulder peak, the initial temperature of the endothermic peak is 251.55±3° C. (preferably ±2° C. or ±1° C.), and the shoulder peak temperature is 241.67±3° C. (preferably ±2° C. or ±1° C.); and/or d) in the DVS pattern, the polymorphic Form I absorbs moisture <2% under 80% RH.

In another preferred embodiment, the polymorphic Form I has one or more features selected from the group consisting of:

1) the polymorphic Form I has an X-ray powder diffraction pattern substantially as shown in curve 1 in FIG. 6;

2) the polymorphic Form I has a TGA pattern substantially as shown in TGA curve in FIG. 8;

3) the polymorphic Form I has a DSC pattern substantially as shown in DSC curve in FIG. 8;

4) the polymorphic Form I has a DVS pattern substantially as shown in FIG. 9; and/or 5) the polymorphic Form I has a polarizing microscope analysis pattern substantially as shown in FIG. 7.

In another preferred embodiment, the X-ray powder diffraction pattern of the polymorphic Form II has characteristic peaks at 2θ values of 4.018±0.2 0 8.722±0.2°, 9.382±0.2°, 11.539±0.2°, 17.732±0.2°, 18.038±0.2°, 19.13±0.2°.

In another preferred embodiment, the X-ray powder diffraction pattern of the polymorphic Form II also has characteristic peaks at one or more 2θ values selected from the group consisting of 8.153±0.2°, 9.882±0.2°, 12.333±0.2°, 19.91±0.2°, 20.747±0.2°, 23.638±0.2°, 26.164±0.2°, 28.341±0.2°.

In another preferred embodiment, the polymorphic Form II has one or more features selected from the group consisting of:

a) the polymorphic Form II is anhydrous and solvent-free crystal form;

b) in the TGA pattern, the weight loss of the polymorphic Form II is about 0.01-0.1% from room temperature to 200° C.; and/or c) in the DSC pattern, the polymorphic Form II has an endothermic peak and an exothermic peak, the initial temperature of the endothermic peak is 252.39±3° C. (preferably ±2° C. or ±1° C.), and the initial temperature of the exothermic peak is 151.75±3° C. (preferably ±2° C. or ±1° C.).

In another preferred embodiment, the polymorphic Form II has one or more features selected from the group consisting of:

1) the polymorphic Form II has an X-ray powder diffraction pattern substantially as shown in curve 2 in FIG. 11;

2) the polymorphic Form II has a TGA pattern substantially as shown in TGA curve in FIG. 13;

3) the polymorphic Form II has a DSC pattern substantially as shown in DSC curve in FIG. 13; and/or 4) the polymorphic Form II has a polarizing microscope analysis pattern substantially as shown in FIG. 12.

In another preferred embodiment, the X-ray powder diffraction pattern of the polymorphic Form III has characteristic peaks at 2θ values of 3.888±0.2°, 4.247±0.2°, 7.269±0.2°, 10.954±0.2°, 18.343±0.2°, 19.009±0.2°, 22.04±0.2°.

In another preferred embodiment, the X-ray powder diffraction pattern of the polymorphic Form III also has characteristic peaks at one or more 2θ values selected from the group consisting of 8.251±0.2°, 8.589±0.2°, 10.352±0.2°, 11.248±0.2°, 17.248±0.2°, 17.855±0.2°, 18.068±0.2°, 19.605±0.2°.

In another preferred embodiment, the polymorphic Form III has one or more features selected from the group consisting of:

a) the polymorphic Form III is an EtOH solvate of compound I;

b) in the TGA pattern, the weight loss of the polymorphic Form III is about 3.0-3.5% from room temperature to 200° C.;

c) the polarizing microscope analysis pattern of the polymorphic Form III is shown as a needle crystal; and/or d) in the DSC pattern, the polymorphic Form III has endothermic peaks with initial temperatures of 105.64±3° C. (preferably ±2° C. or ±1° C.) and 254±3° C. (preferably ±2° C. or ±1° C.), respectively.

In another preferred embodiment, the polymorphic Form III has one or more features selected from the group consisting of:

1) in the polymorphic Form III, the molar ratio of EtOH to compound I is 1:0.25-0.35, preferably 10:3;

2) the polymorphic Form III has an X-ray powder diffraction pattern substantially as shown in curve 3 in FIG. 15;

3) the polymorphic Form III has a TGA pattern substantially as shown in TGA curve in FIG. 17; and/or 4) the polymorphic Form III has a DSC pattern substantially as shown in DSC curve in FIG. 17.

In another preferred embodiment, the DSC pattern of the polymorphic Form III also has an endothermic peak of 211.79±3° C. (preferably ±2° C. or ±1° C.).

In another preferred embodiment, the polymorphic Form III has a polarizing microscope analysis pattern substantially as shown in FIG. 16.

In another preferred embodiment, the X-ray powder diffraction pattern of the polymorphic Form IV has characteristic peaks at 2θ values of 8.529±0.2°, 9.177±0.2°, 9.696±0.2°, 11.324±0.2°, 17.556±0.2°, 17.824±0.2°, 28.107±0.2°.

In another preferred embodiment, the X-ray powder diffraction pattern of the polymorphic Form IV also has characteristic peaks at one or more 2θ values selected from the group consisting of 5.518±0.2°, 7.903±0.2°, 12.152±0.2°, 17.338±0.2°, 18.085±0.2°, 18.909±0.2°, 20.547±0.2°, 25.955±0.2°.

In another preferred embodiment, the polymorphic Form IV has one or more features selected from the group consisting of:

a) the polymorphic Form IV is a hydrate of compound I;

b) in the TGA pattern, the weight loss of the polymorphic Form IV is about 4.6-5.0% from room temperature to 200° C.

In another preferred embodiment, the polymorphic Form IV has one or more features selected from the group consisting of:

1) in the polymorphic Form IV, the molar ratio of water to compound I is 1:0.95-1.05, more preferably 1:1;

2) the polymorphic Form IV has an X-ray powder diffraction pattern substantially as shown in FIG. 21;

3) the polymorphic Form IV has a TGA pattern substantially as shown in TGA curve in FIG. 22; and/or 4) the polymorphic Form IV has a DSC pattern substantially as shown in DSC curve in FIG. 22.

In another preferred embodiment, the DSC pattern of polymorphic Form IV has two broad endothermic peaks and one exothermic peak.

In another preferred embodiment, the X-ray powder diffraction pattern of the polymorphic Form V has characteristic peaks at 2θ values of 7.335±0.2°, 8.304±0.2°, 11.01±0.2°, 14.733±0.2°, 15.132±0.2°, 19.142±0.2°, 22.2±0.2°.

In another preferred embodiment, the X-ray powder diffraction pattern of the polymorphic Form V also has characteristic peaks at one or more 2θ values selected from the group consisting of 4.248±0.2°, 7.712±0.2°, 8.643±0.2°, 11.272±0.2°, 16.712±0.2°, 18.402±0.2°, 30.318±0.2°, 30.621±0.2°.

In another preferred embodiment, the polymorphic Form V has one or more features selected from the group consisting of:

a) the polymorphic Form V is an EtOH solvate of compound I;
b) in the TGA pattern, the weight loss of the polymorphic Form V is about 8.5-8.9% under 180° C.; and/or
c) in the DSC pattern, the polymorphic Form V has 3 endothermic peaks with initial temperatures of 59.19±3° C. (preferably ±2° C. or ±1° C.), 103.16±3° C. (preferably ±2° C. or ±1° C.) and 237.82±3° C. (preferably ±2° C. or ±1° C.), respectively.

In another preferred embodiment, the polymorphic Form V has one or more features selected from the group consisting of:

1) in the polymorphic Form V, the molar ratio of EtOH to compound I is 1:0.45-0.55, preferably 2:1;
2) the polymorphic Form V has an X-ray powder diffraction pattern substantially as shown in curve 5 in FIG. 23;
3) the polymorphic Form V has a TGA pattern substantially as shown in TGA curve in FIG. 24; and/or
4) the polymorphic Form V has a DSC pattern substantially as shown in DSC curve in FIG. 24.

In another preferred embodiment, the X-ray powder diffraction pattern of the polymorphic Form VI has characteristic peaks at 2θ values of 8.839±0.2°, 11.326±0.2°, 16.638±0.2°, 17.474±0.2°, 17.827±0.2°, 18.799±0.2°, 21.306±0.2°.

In another preferred embodiment, the X-ray powder diffraction pattern of the polymorphic Form VI also has characteristic peaks at one or more 2θ values selected from the group consisting of 9.918±0.2°, 10.772±0.2°, 12.948±0.2°, 17.11±0.2°, 19.215±0.2°, 21.608±0.2°, 22.86±0.2°, 26.908±0.2°.

In another preferred embodiment, the polymorphic Form VI has one or more features selected from the group consisting of:

a) the polymorphic Form VI is a DMF solvate of compound I;
b) in the TGA pattern, the weight loss of the polymorphic Form VI is about 1.4-1.6% from room temperature to 200° C.;
c) in the DSC pattern, the polymorphic Form VI has an endothermic peak with initial temperatures of 251.8±3° C. (preferably ±2° C. or ±1° C.), and a exothermic peak with initial temperatures of 214.14±3° C. (preferably ±2° C. or ±1° C.), respectively;
d) the polarizing microscope analysis diagram of the polymorphic Form VI is shown as small particle crystals; and/or
e) the DSC pattern of the polymorphic Form VI also has endothermic peaks with initial temperatures of 91-94° C. and 179-181° C., respectively.

In another preferred embodiment, the polymorphic Form VI has one or more features selected from the group consisting of:

1) in the polymorphic Form VI, the molar ratio of DMF to compound I is 1:0.09-0.11, more preferably 1:0.1;
2) the polymorphic Form VI has an X-ray powder diffraction pattern substantially as shown in curve 6 in FIG. 27;
3) the polymorphic Form VI has a TGA pattern substantially as shown in TGA curve in FIG. 29; and/or
4) the polymorphic Form VI has a DSC pattern substantially as shown in DSC curve in FIG. 29.

In the second aspect of the present invention, it provides a pharmaceutical composition, comprising:

(a) active ingredient: the active ingredient comprises a polymorph of the compound of formula I, wherein the polymorph is selected from the group consisting of polymorphic Form I, polymorphic Form II, polymorphic Form III, polymorphic Form IV, polymorphic Form V, polymorphic Form VI, or a combination thereof; and
(B) pharmaceutically acceptable carriers.

In another preferred embodiment, in the active ingredient, the polymorphic Form I is 50-100 wt %, preferably 70-99.5 wt %, more preferably 80-99 wt %.

In another preferred embodiment, in the active ingredient, the polymorphic Form II is 50-100 wt %, preferably 70-99.5 wt %, more preferably 80-99 wt %.

In the third aspect of the present invention, it provides a use of the polymorph of the compound of formula I according to the first aspect of the present invention or the pharmaceutical composition according to the second aspect of the present invention for the preparation of a medicine or formulation for the prevention and/or treatment of a disease mediated by EP4 receptor activation.

In another preferred embodiment, the disease mediated by EP4 receptor activation is selected from the group consisting of liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, Lymphoma, cervical cancer and other malignant tumors, allergies, inflammation, bone diseases, acute or chronic pain, or a combination thereof.

In the fourth aspect of the present invention, it provides a method for preparing the polymorphic Form I of the compound of formula I, comprising the steps of: providing a mixed solution of the compound of formula I in a first solvent, and slurrying, stirring or volatilizing, so as to obtain the polymorphic Form I, wherein, the first solvent is selected from the group consisting of methanol, isopropanol, isobutanol, 2-butanone, acetonitrile, methyl tert-butyl ether, water, ethyl acrylate, acetone, isopropyl acetate, dichloromethane, n-heptane, 1,4-dioxane, butyl acetate, 4-methyl-2-pentanone, toluene, 2-butanone, cyclohexane, a mixed solution of THF and water, or a combination thereof, preferably methanol or acetone.

In another preferred embodiment, when the first solvent is a mixed solution of THF and water, the volume proportion of THF in the mixed solution is less than 40%, preferably less than 30%, more preferably less than 25%, and most preferably 20%.

In another preferred embodiment, the preparation method of polymorphic Form I has one or more features selected from the group consisting of:

i) the mass volume ratio (g/mL) of the raw material to the first solvent is 1:3-50, preferably 1:5-40, preferably 1:8-35;
ii) the raw material is selected from the group consisting of amorphous compound of formula I, crystal form, or a combination thereof;
iii) the slurrying or stirring time is 0.5-24 h, preferably, 1-12 h, more preferably, 2-6 h; and/or
iv) the temperature of slurrying, stirring or volatilizing is 0-100° C., preferably 10-80° C., more preferably 15-70° C., and most preferably 20-65° C.

In the fifth aspect of the present invention, it provides a method for preparing the polymorphic Form II of the compound of formula I, comprising the steps of: providing a suspension of the compound of formula I in ethanol, stirring the suspension at 4-40° C. and separating to obtain the polymorphic Form II.

In another preferred embodiment, in the preparation method of polymorphic Form II, the stirring has one or more features selected from the group consisting of:

1) the stirring time is 6 h-5 days, preferably, 12 h-4 days, more preferably, 1-4 days, most preferably, 2-4 days; and/or 2) in another preferred embodiment, the stirring temperature is 10-30° C., more preferably, 25±5° C.

In another preferred embodiment, the preparation method of the polymorphic Form II of the compound of formula I comprises the steps of: providing a saturated solution of the compound of formula I in ethanol, undergoing cooling crystallization, and separating to obtain the polymorphic Form II.

In another preferred embodiment, the saturated solution is a hot saturated solution of 40-80° C., preferably 45-60° C.

In another preferred embodiment, the cooling crystallization is a natural condition that drops to room temperature.

In the fifth aspect of the present invention, it provides a method for preparing the polymorphic Form III of the compound of formula I, comprising the steps of: providing a suspension of the compound of formula I in ethanol, stirring or slurrying the suspension at 45-65° C. and separating to obtain the polymorphic Form III.

In another preferred embodiment, the preparation method of the polymorphic Form III has one or more features selected from the group consisting of:

i) the stirring temperature is 50-60° C., preferably 50-55° C.; and/or ii) the stirring time is 0.5-3 days, preferably 1-2 days.

In the sixth aspect of the present invention, it provides a method for preparing the polymorphic Form IV of the compound of formula I, comprising the steps of: providing a mixed solution of the compound of formula I in methanol, and volatilizing the mixed solution at room temperature to obtain the polymorphic Form IV.

In another preferred embodiment, the preparation method of the polymorphic Form IV of the compound of formula I comprises the steps of: providing a mixed solution of the compound of formula I in methanol, adding water to the mixed solution and volatilizing in a room temperature environment to obtain the polymorphic Form IV.

In another preferred embodiment, in the mixed solution, the concentration of the compound of formula I is 8-20 mg/mL.

In another preferred embodiment, the mixed solution does not contain the compound I in solid form, preferably, the mixed solution is a saturated solution of the compound of formula I.

In the seventh aspect of the present invention, it provides a method for preparing the polymorphic Form V of the compound of formula I, comprising the steps of: providing a mixed solution of the compound of formula I in ethanol, and volatilizing the solvent at room temperature to obtain the polymorphic Form V.

In another preferred embodiment, the preparation method of the polymorphic Form V of the compound of formula I comprises the steps of: providing a mixed solution of the compound of formula I in ethanol, adding methanol to the mixture and volatilizing the solvent at room temperature to obtain the polymorphic Form V.

In another preferred embodiment, the ratio of methanol to ethanol is 1:0.5-10, preferably 1:0.5-5.

In another preferred embodiment, the mixed solution does not contain the compound I in solid form, preferably, the mixed solution is a saturated solution of the compound of formula I.

In the eighth aspect of the present invention, it provides a method for preparing the polymorphic Form VI of the compound of formula I, comprising the steps of: providing a suspension of the compound of formula I in a mixed solvent consisting of DMF and $H_2O$, stirring the obtained suspension, and separating to obtain the polymorphic Form VI.

In another preferred embodiment, the preparation method of the polymorphic Form VI has one or more features selected from the group consisting of:

i) in the mixed solvent of DMF and $H_2O$, the volume ratio of DMF to $H_2O$ is 1:0.5-2, preferably 1:0.8-1.2, more preferably 1:1;

ii) the stirring temperature is 40-80° C., preferably 50-70° C., more preferably 60-70° C.;

iii) the stirring time is 1-5 days, preferably 2-4 days.

In the ninth aspect of the present invention, it provides a method for preventing and/or treating a disease mediated by EP4 receptor activation, the method comprises the step of: administering to a subject in need thereof a therapeutically effective amount of at least one polymorph of the compound of formula I according to the first aspect of the present invention or the pharmaceutical composition according to the second aspect of the present invention.

In another preferred embodiment, the subject is mammal.

In another preferred embodiment, the subject is selected from the group consisting of a human, a mouse, a cat, and a dog.

It should be understood that within the scope of the present invention, the above-mentioned technical features of the present invention and the technical features specifically described in the following (such as examples) can be combined with each other to form a new or preferred technical solution. Limited to space, it is not repeated here.

DETAILED DESCRIPTION OF THE INVENTION

Figure 1:
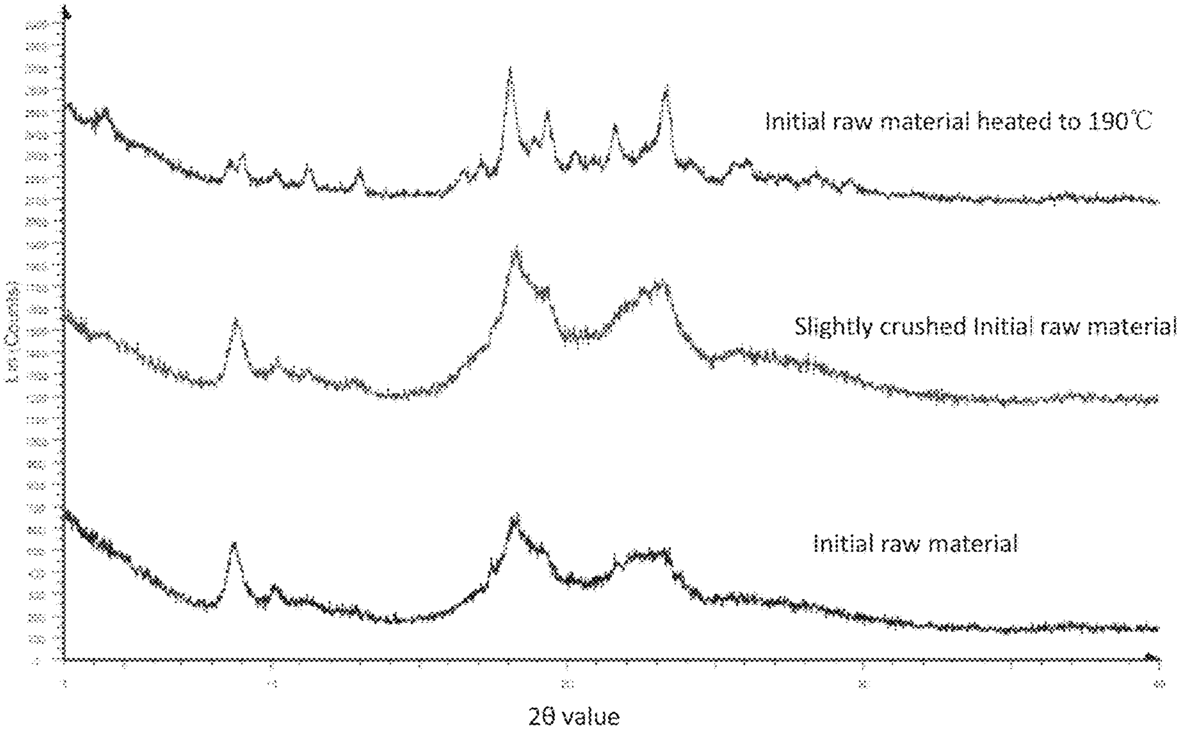
FIG. 1 is an X-ray powder diffraction pattern of the initial raw material.

After an extensively and intensively study, and by extensive screening and testing, the present inventors obtained a polymorph of the EP4 receptor antagonist (S)-4-(1-(2-(4-fluorobenzyl)-4,7-dihydro-5H-thieno [2,3-c] pyran-3-formamido) ethyl) benzoic acid for the first time. Surprisingly, the polymorph of the present invention has excellent stability and is more suitable for drug processing and storage. On this basis, the present invention is completed.

Terms

Unless otherwise defined, all technical and scientific terms used herein have the same meaning as normally be understood by those of ordinary skill in the art to which the present invention belongs.

As used herein, the term "about" is intended to mean that the value can vary from the enumerated value by no more than 1% when used in reference to a specific enumerated value. For example, as used herein, the expression "about 100" includes all values between 99 and 101 (e.g., 99.1, 99.2, 99.3, 99.4, etc.).

As used herein, the terms "contain" or "include (comprise)" may be open-ended, semi-closed, and closed-ended. In other words, the term also includes "essentially consist of", or "consist of".

As used herein, the terms "polymorph", "polymorphic Form", and "crystal form" are used interchangeably to refer to a substance in crystalline form.

As used herein, the term "room temperature" refers to a temperature of 4-40° C., preferably 25±5° C.

As used herein, the term "n or more" refers to including n and any positive integer greater than n (e.g., n, n+1, . . . ), where the upper limit Nup is the number of all values in the group. For example, "1 or more" does not only include each positive integer of 1, 2, 3, 4, 5, 6, 7, 8, 9, 10 . . . and the upper limit Nup, but also includes ranges such as "2 or more", "3 or more", "4 or more", "5 or more", "6 or more", "7 or more", "8 or more", "9 or more", "10 or more", etc. . . . .

Active Ingredient

As used herein, the term "active ingredient" or "active compound" refers to (S)-4-(1-(2-(4-fluorobenzyl)-4,7-dihydro-5H-thieno [2,3-c] pyran-3-formamido) ethyl) benzoic acid (compound of formula I), in particular the compound of formula I in the form of a polymorph of the present invention, such as polymorphic Form I, II, III, IV, V, VI, or a combination thereof.

Preferably, in the active ingredient, the polymorphic Form I is 50-100 wt %, preferably 70-99.5 wt %, more preferably 80-99 wt %.

Polymorph

Through experiment, the present invention found that (S)-4-(1-(2-(4-fluorobenzyl)-4,7-dihydro-5H-thieno [2,3-c] pyran-3-formamido) ethyl) benzoic acid has polymorphic Form I, II, III, IV, V, VI. Among the six polymorphic Forms, polymorphic Form I and polymorphic Form II are anhydrous polymorphs; polymorphic Form III, polymorphic Form V and polymorphic Form VI are solvent crystal forms; and polymorphic Form IV is hydrate.

Polymorphic Form I

The X-ray powder diffraction pattern of the polymorphic Form I has characteristic peaks at 2θ values of 4.234±0.2°, 8.505±0.2°, 8.96±0.2°, 11.177±0.2°, 12.892±0.2°, 18.05±0.2°, 23.333±0.2°.

In another preferred embodiment, the X-ray powder diffraction pattern of the polymorphic Form I also has characteristic peaks at one or more 2θ values selected from the group consisting of 10.05±0.2°, 16.438±0.2°, 17.093±0.2°, 19.229±0.2°, 20.259±0.2°, 21.544±0.2°, 25.613±0.2°, 26.051±0.2°.

In another preferred embodiment, the X-ray powder diffraction pattern of the polymorphic Form I also has characteristic peaks at one or more 2θ values selected from the group consisting of 18.851±0.2°, 19.406±0.2°, 22±0.2°, 22.543±0.2°, 24.285±0.2°, 26.774±0.2°, 27.331±0.2°, 28.441±0.2°, 29.04±0.2°, 29.529±0.2° 30.185±0.2°, 33.196±0.2°, 34.049±0.2°, 34.714±0.2°, 36.109±0.2°, 37.076±0.2°, 38.936±0.2°.

Polymorphic Form I can be prepared by the following methods:

- providing a mixed solution of the compound of formula I in a first solvent, and slurrying, stirring or volatilizing, so as to obtain the polymorphic Form I, wherein,
- the first solvent is selected from the group consisting of methanol, isopropanol, isobutanol, 2-butanone, acetonitrile, methyl tert-butyl ether, water, ethyl acrylate, acetone, isopropyl acetate, dichloromethane, n-heptane, 1,4-dioxane, butyl acetate, 4-methyl-2-pentanone, toluene, 2-butanone, cyclohexane, a mixed solution of THF and water, or a combination thereof, preferably methanol or acetone.

In another preferred embodiment, when the first solvent is a mixed solution of THF and water, the volume proportion of THF in the mixed solution is less than 40%, preferably less than 30%, more preferably less than 25%, and most preferably 20%.

In another preferred embodiment, the preparation method of polymorphic Form I has one or more features selected from the group consisting of:

i) the mass volume ratio (g/mL) of the raw material to the first solvent is 1:3-50, preferably 1:5-40, preferably 1:8-35;

ii) the raw material is selected from the group consisting of amorphous compound of formula I, crystal form, or a combination thereof;

iii) the slurrying or stirring time is 0.5-24 h, preferably, 1-12 h, more preferably, 2-6 h; and/or iv) the temperature of slurrying, stirring or volatilizing is 0-100° C., preferably 10-80° C., more preferably 15-70° C., and most preferably 20-65° C.

It is shown by DSC heat treatment as well as polymorphic Form I and crystal transformation experiments that polymorphic Form I is a stable polymorphic Form.

Polymorphic Form II

In another preferred embodiment, the X-ray powder diffraction pattern of the polymorphic Form II has characteristic peaks at 2θ values of 4.018±0.2 0 8.722±0.2° 9.382±0.2°, 11.539±0.2°, 17.732±0.2°, 18.038±0.2°, 19.13±0.2°.

In another preferred embodiment, the X-ray powder diffraction pattern of the polymorphic Form II also has characteristic peaks at one or more 2θ values selected from the group consisting of 8.153±0.2°, 9.882±0.2°, 12.333±0.2°, 19.91±0.2°, 20.747±0.2°, 23.638±0.2°, 26.164±0.2°, 28.341±0.2°.

A method for preparing the polymorphic Form II, comprising the steps of: providing a suspension of the compound of formula I in ethanol, stirring the suspension at 4-40° C. and separating to obtain the polymorphic Form II.

In another preferred embodiment, in the preparation method for polymorphic Form II, the stirring has one or more features selected from the group consisting of: 1) the stirring time is 6 h-5 days, preferably, 12 h-4 days, more preferably, 1-4 days, most preferably, 2-4 days; and/or 2) the stirring temperature is 10-30° C., more preferably, 25±5° C.

Another preparation method of the polymorphic Form II of the compound of formula I comprises the steps of: providing a saturated solution of the compound of formula I in ethanol, cooling and crystallizing, and separating to obtain the polymorphic Form II.

In another preferred embodiment, the saturated solution is a hot saturated solution of 40-80° C., preferably 45-60° C.

In another preferred embodiment, the cooling and crystallizing is a natural condition that drops to room temperature.

Polymorphic Form III

In another preferred embodiment, the X-ray powder diffraction pattern of the polymorphic Form III has characteristic peaks at 2θ values of 3.888±0.2°, 4.247±0.2°, 7.269±0.2°, 10.954±0.2°, 18.343±0.2°, 19.009±0.2°, 22.04±0.2°.

In another preferred embodiment, the X-ray powder diffraction pattern of the polymorphic Form III also has characteristic peaks at one or more 2θ values selected from the group consisting of 8.251±0.2°, 8.589±0.2°, 10.352±0.2°, 11.248±0.2°, 17.248±0.2°, 17.855±0.2°, 18.068±0.2°, 19.605±0.2°.

The polymorphic Form III is an EtOH solvate of Compound I; preferably, in the polymorphic Form III, the molar ratio of EtOH to Compound I is 1:0.25-0.35, preferably 10:3.

The preparation method for polymorphic Form III comprises the steps of: providing a suspension of the compound of formula I in ethanol, stirring or slurrying the suspension at 45-65° C. and separating to obtain the polymorphic Form III.

In another preferred embodiment, the preparation method for the polymorphic Form III has one or more features selected from the group consisting of:

i) the stirring temperature is 50-60° C., preferably 50-55° C.; and/or ii) the stirring time is 0.5-3 days, preferably 1-2 days.

Polymorphic Form IV

In another preferred embodiment, the X-ray powder diffraction pattern of the polymorphic Form IV has characteristic peaks at 2θ values of 8.529±0.2°, 9.177±0.2°, 9.696±0.2°, 11.324±0.2°, 17.556±0.2°, 17.824±0.2°, 28.107±0.2°.

In another preferred embodiment, the X-ray powder diffraction pattern of the polymorphic Form IV also has characteristic peaks at one or more 2θ values selected from the group consisting of 5.518±0.2°, 7.903±0.2°, 12.152±0.2°, 17.338±0.2°, 18.085±0.2°, 18.909±0.2°, 20.547±0.2°, 25.955±0.2°.

The polymorphic Form IV is a hydrate of the compound I; preferably, in the polymorphic Form IV, the molar ratio of water to compound I is 1:0.95-1.05, more preferably 1:1.

The preparation method for polymorphic Form IV comprises the steps of: providing a mixed solution of the compound of formula I in methanol, and volatilizing the mixed solution at room temperature to obtain the polymorphic Form IV.

In another preferred embodiment, the preparation method for the polymorphic Form IV of the compound of formula I comprises the steps of: providing a mixed solution of the compound of formula I in methanol, adding water to the mixed solution and volatilizing in a room temperature environment to obtain the polymorphic Form IV.

In another preferred embodiment, in the mixed solution, the concentration of the compound of formula I is 8-20 mg/mL.

In another preferred embodiment, the mixed solution does not contain the compound I in solid form, preferably, the mixed solution is a saturated solution of the compound of formula I.

Polymorphic Form V

In another preferred embodiment, the X-ray powder diffraction pattern of the polymorphic Form V has characteristic peaks at 2θ values of 7.335±0.2°, 8.304±0.2°, 11.01±0.2°, 14.733±0.2°, 15.132±0.2°, 19.142±0.2°, 22.2±0.2°.

In another preferred embodiment, the X-ray powder diffraction pattern of the polymorphic Form V also has characteristic peaks at one or more 2θ values selected from the group consisting of 4.248±0.2°, 7.712±0.2°, 8.643±0.2°, 11.272±0.2°, 16.712±0.2°, 18.402±0.2°, 30.318±0.2°, 30.621±0.2°.

The polymorphic Form V is an EtOH solvate of Compound I; preferably, in the polymorphic Form V, the molar ratio of EtOH to Compound I is 1:0.45-0.55, preferably 2:1.

The preparation method of the polymorphic Form V comprises the steps of: providing a mixed solution of the compound of formula I in ethanol, and volatilizing the solvent at room temperature to obtain the polymorphic Form V.

Another preparation method for the polymorphic Form V of the compound of formula I comprises the steps of: providing a mixed solution of the compound of formula I in ethanol, adding methanol to the mixture and volatilizing the solvent at room temperature to obtain the polymorphic Form V.

In another preferred embodiment, the ratio of methanol to ethanol is 1:0.5-10, preferably 1:0.5-5.

In another preferred embodiment, the mixed solution does not contain the compound I in solid form, preferably, the mixed solution is a saturated solution of the compound of formula I.

Polymorphic Form VI

In another preferred embodiment, the X-ray powder diffraction pattern of the polymorph VI has characteristic peaks at 2θ values of 8.839±0.2°, 11.326±0.2°, 16.638±0.2°, 17.474±0.2°, 17.827±0.2°, 18.799±0.2°, 21.306±0.2°.

In another preferred embodiment, the X-ray powder diffraction pattern of the polymorphic Form VI also has characteristic peaks at one or more 2θ values selected from the group consisting of 9.918±0.2°, 10.772±0.2°, 12.948±0.2°, 17.11±0.2°, 19.215±0.2°, 21.608±0.2°, 22.86±0.2°, 26.908±0.2°.

The polymorphic Form VI is a DMF solvate of Compound I; preferably, in the polymorphic Form VI, the molar ratio of DMF to compound I is 1:0.09-0.11, more preferably, 1:0.1. The preparation method for polymorphic Form VI comprises the steps of: providing a suspension of the compound of formula I in a mixed solvent consisting of DMF and $H_2O$, stirring the obtained suspension, and separating to obtain the polymorphic Form VI.

In another preferred embodiment, the preparation method of the polymorphic Form VI has one or more features selected from the group consisting of:

i) in the mixed solvent of DMF and $H_2O$, the volume ratio of DMF to $H_2O$ is 1:0.5-2, preferably 1:0.8-1.2, more preferably 1:1;

ii) the stirring temperature is 40-80° C., preferably 50-70° C., more preferably 60-70° C.;

iii) the stirring time is 1-5 days, preferably 2-4 days.

Pharmaceutical Compositions and Methods of Administration

Since the polymorphs of the present invention is a highly active, highly selective prostaglandin E2 receptor EP4 antagonist. The polymorphs of the present invention, as well as pharmaceutical compositions containing the polymorphs of the present invention as the main active ingredient, are therefore useful for the treatment, prevention and alleviation of diseases and disorders mediated by EP4 receptor activation. According to the prior art, the polymorphs of the present invention is useful in the treatment of the following diseases (but not limited to) liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, Lymphoma, cervical cancer and other malignant tumors, allergies, inflammation, bone diseases, acute or chronic pain, or a combination thereof.

The pharmaceutical composition of the present invention comprises a polymorph of the present invention and a pharmaceutically acceptable excipient or carrier within a safe and effective amount range.

Among them, "safe and effective amount" refers to an amount of a compound (or polymorph) that is sufficient to significantly improve the condition without causing serious side effects. Typically, the pharmaceutical composition contains 1-2000 mg of the polymorph of the present invention/dose, and more preferably 10-200 mg of the polymorph of the present invention/dose. Preferably, the "one dose" is a capsule or tablet.

"Pharmaceutically acceptable carrier" refers to one or more compatible solid or liquid fillers or gels suitable for human use and with sufficient purity and low enough toxicity. "Compatibility" herein refers to the ability of components of a composition to blend with the active ingredient of the invention and with each other, without significantly reducing the efficacy of the active ingredient. Examples of pharmaceutically acceptable carriers include cellulose and its derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oil (such as soybean oil, sesame oil, peanut oil, olive oil, etc.), polyols (such as propylene glycol, glycerin, mannitol, sorbitol, etc.), emulsifiers (such as Tween®), wetting agents (such as sodium dodecyl sulfate), colorants, flavoring agents, stabilizers, antioxidants, preservatives, pyrogen-free water, etc.

There are no particular limitations for the methods of administration of the polymorph or pharmaceutical compositions of the present invention, and representative methods of administration include, but are not limited to, oral, intratumoral, rectal, parenteral (intravenous, intramuscular or subcutaneous), and topical administration.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with the following ingredients: (a) filler or compatibilizer, such as microcrystalline cellulose, starch, lactose, sucrose, glucose, mannitol and silicic acid; (b) binders, e.g., hydroxymethylcellulose, alginate, gelatin, polyvinylpyrrolidone, sucrose, and gum arabic; (c) humectants, e.g., glycerol; (d) disintegrants, e.g., agar, calcium carbonate, potato starch or tapioca starch, alginic acid, certain complex silicates, sodium carbonate, crospovidone, sodium croscarmellose; (e) a slow-dissolving reagent, e.g., paraffin; (f) an absorption accelerator, e.g., a quaternary amine compound; (g) a wetting agent, e.g., cetyl alcohol and glyceryl monostearate; (h) an adsorbent, e.g., kaolin; and (i) a lubricant, e.g., talc, calcium stearate, magnesium stearate, solid polyethylene glycol, sodium dodecyl sulfate, and mixtures thereof. In capsules, tablets and pills, dosage forms may also contain buffers.

Solid dosage forms such as tablets, sugar pills, capsules, pills and granules may be prepared using coating and shell materials such as casing and other materials well known in the art. They may comprise an opaque agent, and the release of active ingredient in such a composition may be released in a delayed manner in a part of the digestive tract. Examples of embedding components that can be employed are polymeric substances and wax substances. If necessary, the active ingredient may also form a microcapsule form with one or more of the excipients described above.

Liquid dosage forms for oral administration include pharmaceutically acceptable emulsions, solutions, suspensions, syrups or tinctures. In addition to the active ingredient, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures thereof.

In addition to these inert diluents, the composition may also contain auxiliaries such as wetting agents, emulsifiers, suspending agents, sweeteners, flavoring agents and flavors.

In addition to the active ingredient, the suspensions may comprise suspending agents, for example, ethoxylated isostearyl alcohol, polyoxyethylene sorbitol and sorbitan esters, microcrystalline cellulose, aluminum methanol and agar, or mixtures thereof.

The composition for parenteral injection may comprise physiologically acceptable sterile aqueous or anhydrous solutions, dispersions, suspensions or emulsions, and sterile powders for redissolution into sterile injectable solutions or dispersions. Suitable aqueous and non-aqueous carriers, diluents, solvents, or excipients include water, ethanol, polyols, and suitable mixtures thereof.

The dosage forms of the crystalline forms of the present invention for topical administration include ointments, powder, patches, propellants and inhalants. The active ingredient is mixed under sterile conditions with a physiologically acceptable carrier and any preservatives, buffers or propellants as required.

The polymorphs of the present invention can be administered alone or in combination with other pharmaceutically acceptable compounds.

When a pharmaceutical composition is used, a safe and effective amount of the polymorph of the present invention is applied to a mammal (e.g., a human) in need of treatment at a pharmaceutically effective dose. For a person weighing 60 kg, the daily dose is usually 1 to 2000 mg, preferably 10 to 500 mg. Of course, the specific dosage should also consider the route of administration, the patient's health and other factors, which are within the skill range of skilled doctors.

The Main Advantages of the Present Invention Include:

1. The present invention provides for the first time 6 single polymorphic forms of compound I and a preparation method therefor, including 2 anhydrous polymorphic forms (polymorphic Form I and polymorphic Form II), 3 solvate compounds (polymorphic Form III, polymorphic Form V and polymorphic Form VI) and 1 hydrate (polymorphic Form IV), and the polymorphic form has higher stability (thermal stability, moisture absorption stability) than amorphous form, and is easy to process and more suitable for being prepared into a medicine.
2. polymorphic Form I and II are solvent-free crystal forms, and from the TGA and DSC results, it can be seen that polymorphic Form I and II have better stability than white solids in the prior art, and polymorphic Form I and II are non-agglomerated, easy to disperse, suitable for the preparation process.
3. The polymorphic Form I of the present invention is a thermodynamically stable crystal form of compound I, which has thermal stability, high humidity stability, high purity, good solubility, and has significant advantages in industrial production.

The present invention will be further explained below in conjunction with specific examples. It should be understood that these examples are only used to illustrate the present invention and not to limit the scope of the present invention. The experimental methods that do not indicate specific conditions in the following examples usually follow the conventional conditions, or the conditions suggested by the manufacturer. Unless otherwise specified, percentages and parts are percentages by weight and parts by weight. The raw materials or instruments used in the examples of the present invention, unless otherwise specified, are commercially available.

Analytical Methods and Instruments

Analysis of $^1$H NMR

The structure of the solid sample and the solvent contained in the sample were confirmed by $^1$H NMR. The instrument used for $^1$H NMR analysis is Bruker Advance 300 equipped with B-ACS 120 automatic sampling system.

X-Ray Powder Diffraction (XRPD)

The solid samples obtained from the experiment were analyzed by D8 advance powder X-ray diffraction analyzer (Bruker). The instrument is equipped with a LynxEye detector, and the ray species is Cu Kα ($\lambda$=1.54184 Å). The 2θ scanning range of the sample is from 3° to 40°, and the scanning step is 0.02°. When measuring the sample, the light tube voltage and light tube current were 40 KV and 40 mA respectively.

Polarizing Microscope Analysis (PLM)

The instrument type used for PLM analysis is ECLIPSE LV100POL polarizing microscope (Nikon, Japan).

Thermogravimetric Analysis (TGA)

The model of the thermogravimetric analyzer is TGA Q500(TA, USA). The sample was placed in a balanced open aluminum sample tray, and the mass was automatically weighed in a TGA heating furnace. The sample was heated to the final temperature at a rate of 10° C./min.

Differential Scanning Calorimetry Analysis (DSC)

The instrument model for Differential Scanning Calorimetry is DSC Q200(TA, USA). The sample was accurately weighed and placed in a DSC pierced sample tray, and the accurate quality of the sample was recorded. The sample was heated to the final temperature at a heating rate of 10° C./min.

Dynamic Water Vapor Adsorption (DVS) Method

The instrument model used for dynamic moisture absorption and desorption analysis is IGA Sorp(Hidentity Isochema). The sample measurement adopts gradient mode, the relative humidity range of the test is 0% to 90%, and the humidity increment of each gradient is 10%. The specific parameters are as follows:

Sample temperature: 25° C.
Temperature stability: 0.1° C./min
Flow rate: 250 mL/min
Scan: 2
Model: F1
Minimum time: 30 min
Maximum time: 120 min
Waiting cap: 98%
Start: Adsorption Scan
Adsorption humidity (%):0, 10, 20, 30, 40, 50, 60, 70, 80, 90;
Desorption humidity (%):80, 70, 60, 50, 40, 30, 20, 10, 0.

Example 1

Preparation of Amorphous Compound I (S)-4-(1-(2-(4-fluorobenzyl)-4,7-dihydro-5H-thieno [2,3-c] pyran-3-formamido) ethyl) benzoic acid was prepared by the same method as Examples 1-14 in the publication of the international application with application number of PCT/CN2018/117235. After purification on a silica gel (200-300 mesh) chromatographic column, saturated $Na_2CO_3$ solution was added, the pH was adjusted to 12. The product was dissolved in the aqueous phase, and extracted and separated to obtain an aqueous layer; then 2 mol/L hydrochloric acid was added to the aqueous phase, and the pH was adjusted to 3. The product was precipitated. After filtration, the filter cake was transferred to a vacuum drying oven for 16 h, the temperature was controlled to 55 degrees to obtain compound I (free acid form), as a white solid with purity>99%.

The abovementioned white solids were characterized by XRPD, PLM, TGA and DSC.

Figure 2:
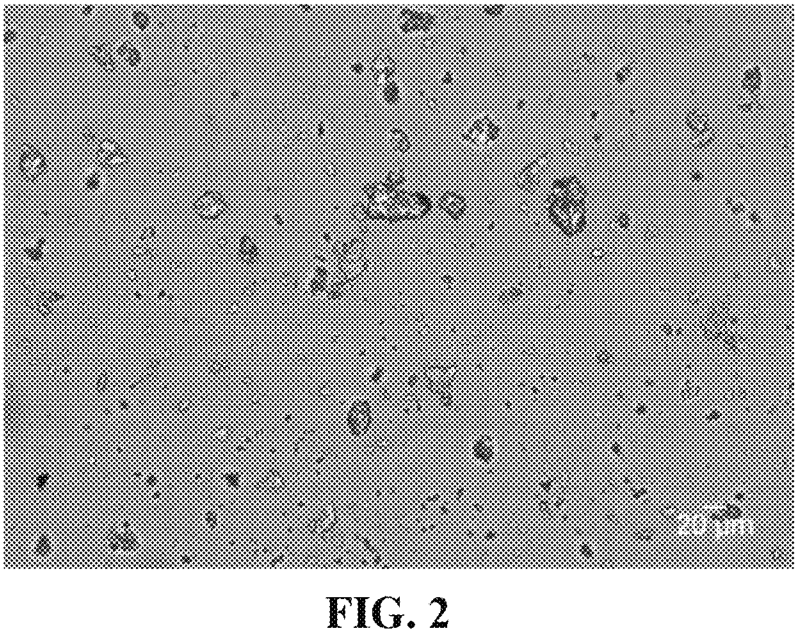
FIG. 2 is a polarizing microscope analysis photograph of the initial raw material.
Figure 3:
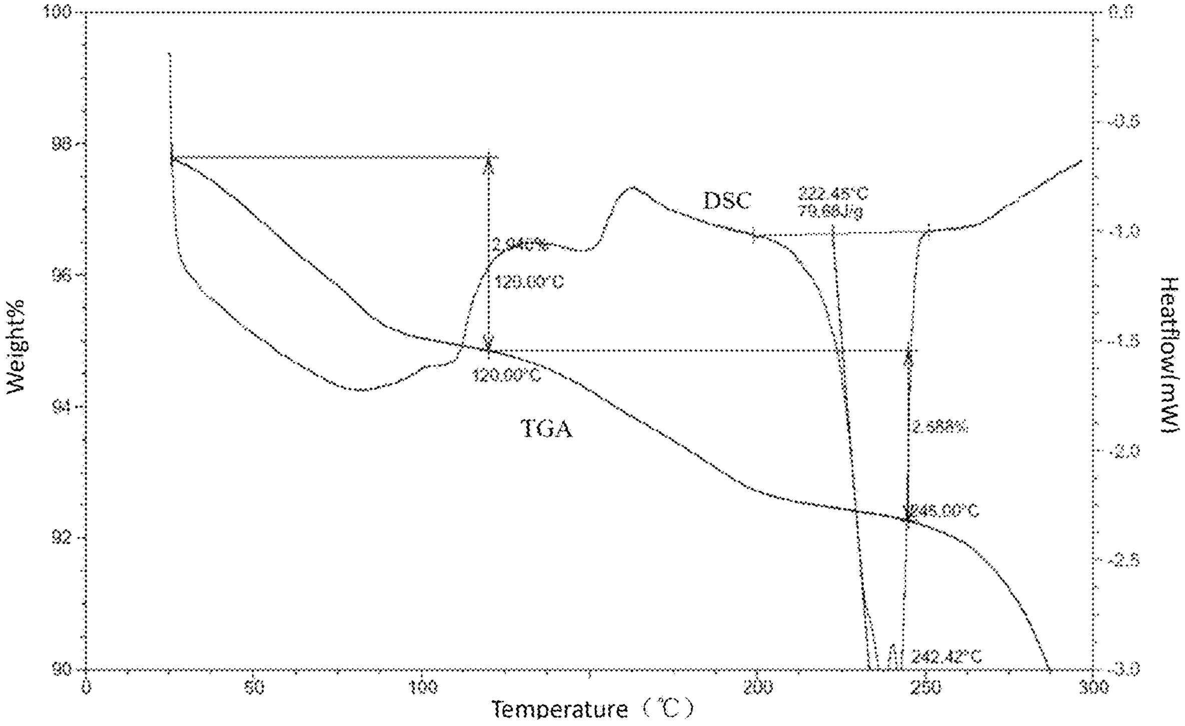
FIG. 3 is a TGA-DSC pattern of the initial raw material.

The results are shown in FIGS. 1-3. From the XRPD curve (FIG. 1—initial raw material curve) and PLM, it can be seen that the resulting white solid is basically amorphous, and there is agglomeration, in preparation, it is not easy to disperse.

TGA (FIG. 2) results show that the white solid has two stages of weight loss (weight loss 2.94% before 120° C. and weight loss 2.59% between 120 and 245° C.) during heating from room temperature to high temperature; DSC has multiple thermal events, and severe exothermic and endothermic events exist below 150° C.

In the following examples, the white solid is used as a raw material for preparing the polymorph (referred to as an initial raw material).

Polymorph Screening of Compound I

Example 2

After the initial raw material of compound I was slightly crushed, XRPD characterization was carried out.

The XRPD results are shown in FIG. 1. According to the corresponding XRPD curve, only substances with very low crystallinity can be obtained by crushing.

The initial raw material of compound I was heated to 190° C. for XRPD, PLM, TGA and DSC characterization.

Figure 4:
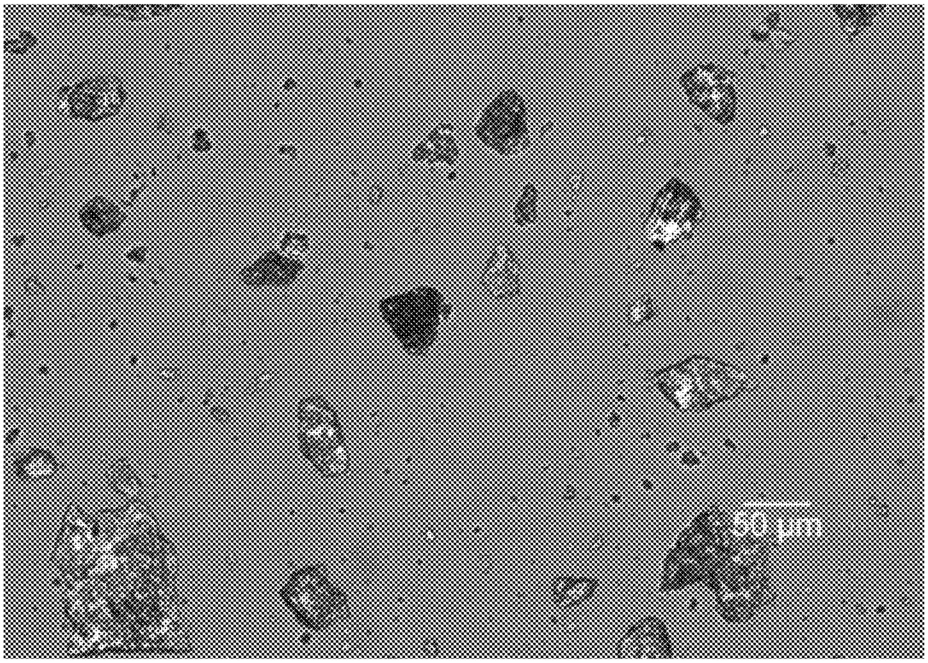
FIG. 4 is a polarizing microscope analysis photograph of the sample obtained by heating the initial raw material to 190° C.
Figure 5:
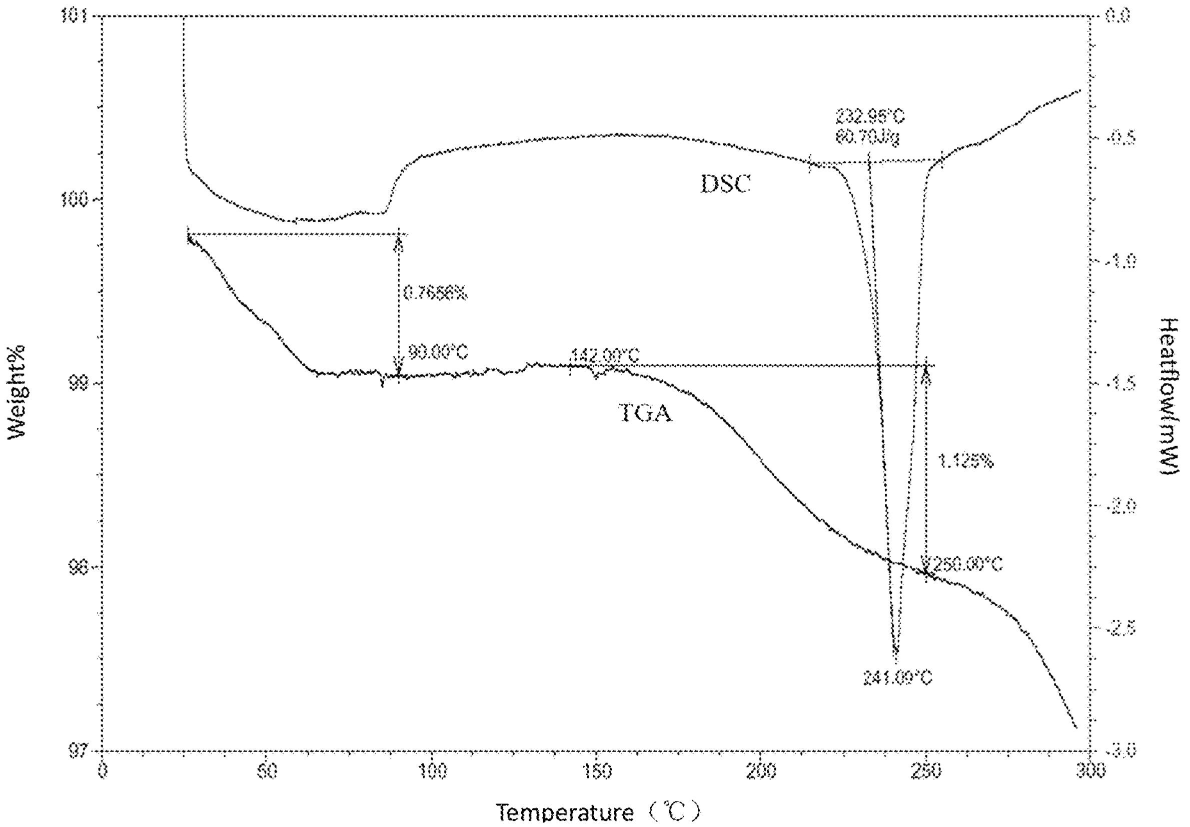
FIG. 5 is a TGA-DSC pattern of the sample obtained by heating the initial raw material to 190° C.

The results are shown in FIGS. 1, 4-5. According to the corresponding XRPD curve in FIG. 1, the compound I with high crystallinity cannot be obtained by heating.

Example 3

The initial raw material of Compound I was slurried in acetone for 4 hours, filtered and the resulting solid was characterized by XRPD, PLM, TGA, DSC and DVS.

Figure 6:
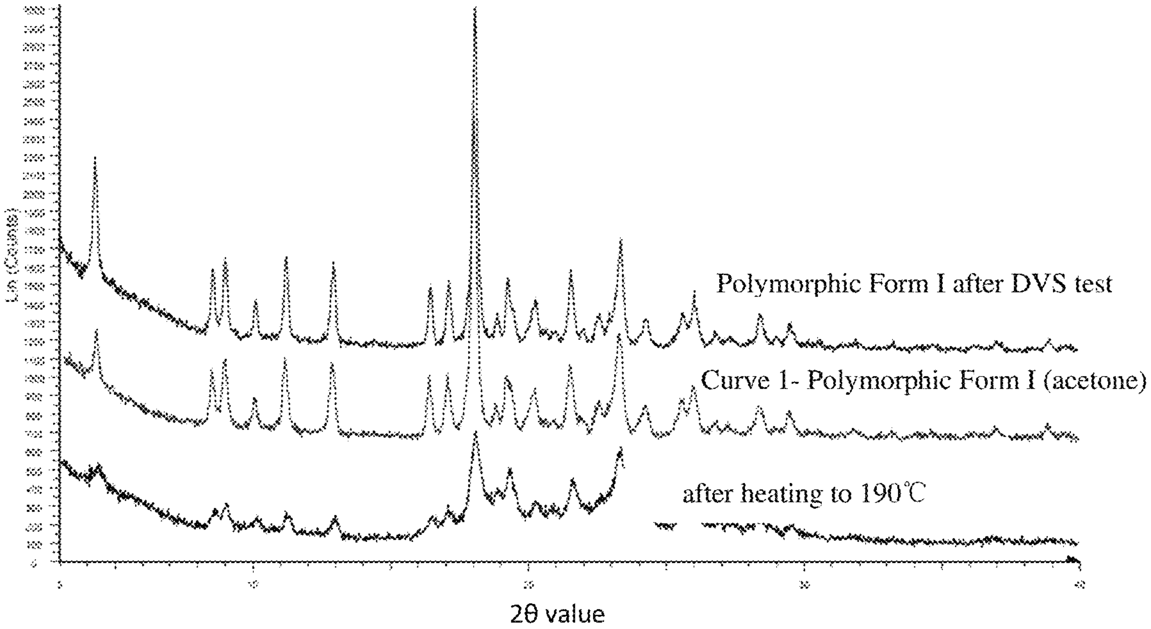
FIG. 6 is an X-ray powder diffraction pattern of polymorphic Form I.

The XRPD results are shown in FIG. 6, and a polymorph with a higher degree of crystallinity is obtained, named as polymorphic Form I.

Figure 7:
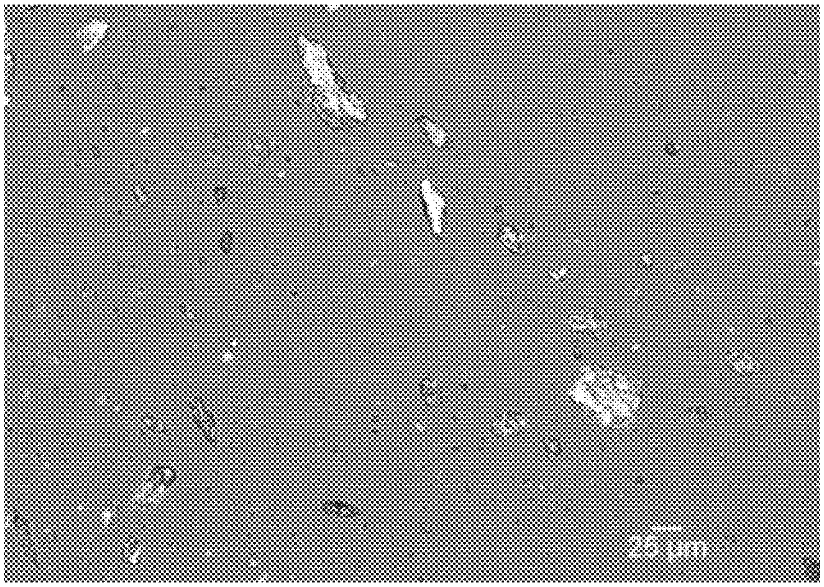
FIG. 7 is a polarizing microscope analysis photograph of polymorphic Form I.
Figure 8:
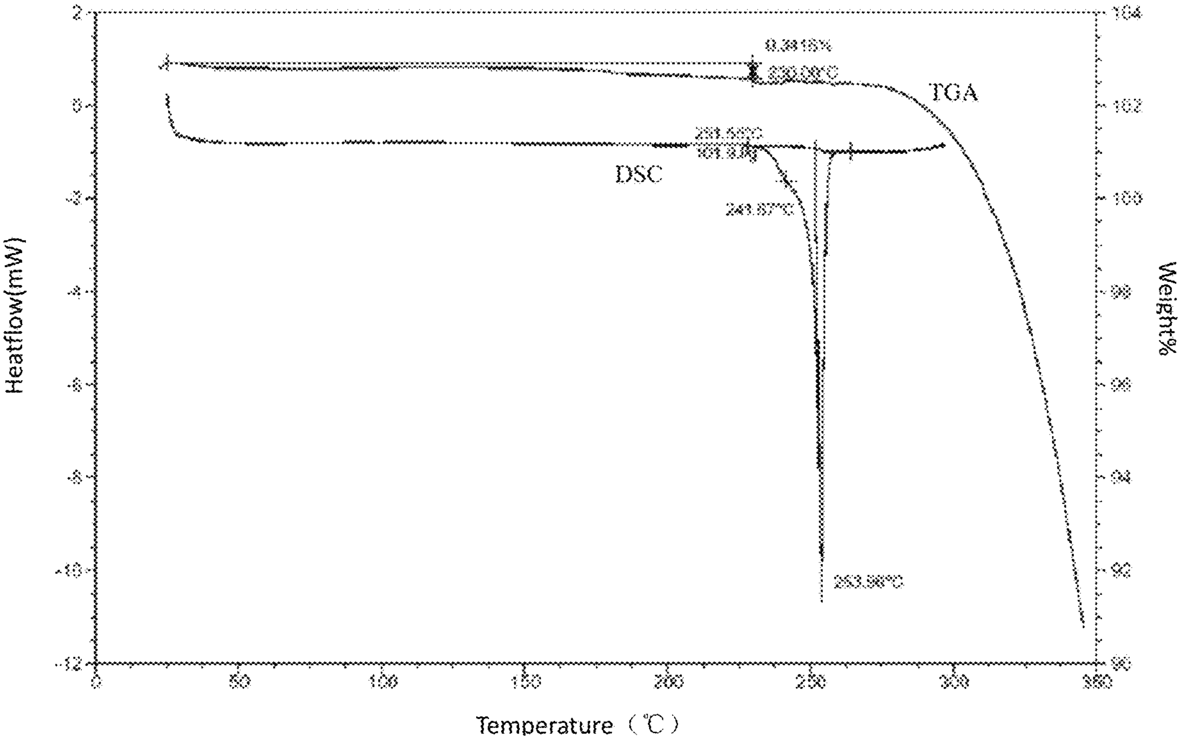
FIG. 8 is a Thermogravimetric Analysis-Differential Scanning Calorimetry (TGA-DSC) pattern for polymorphic Form I.
Figure 9:
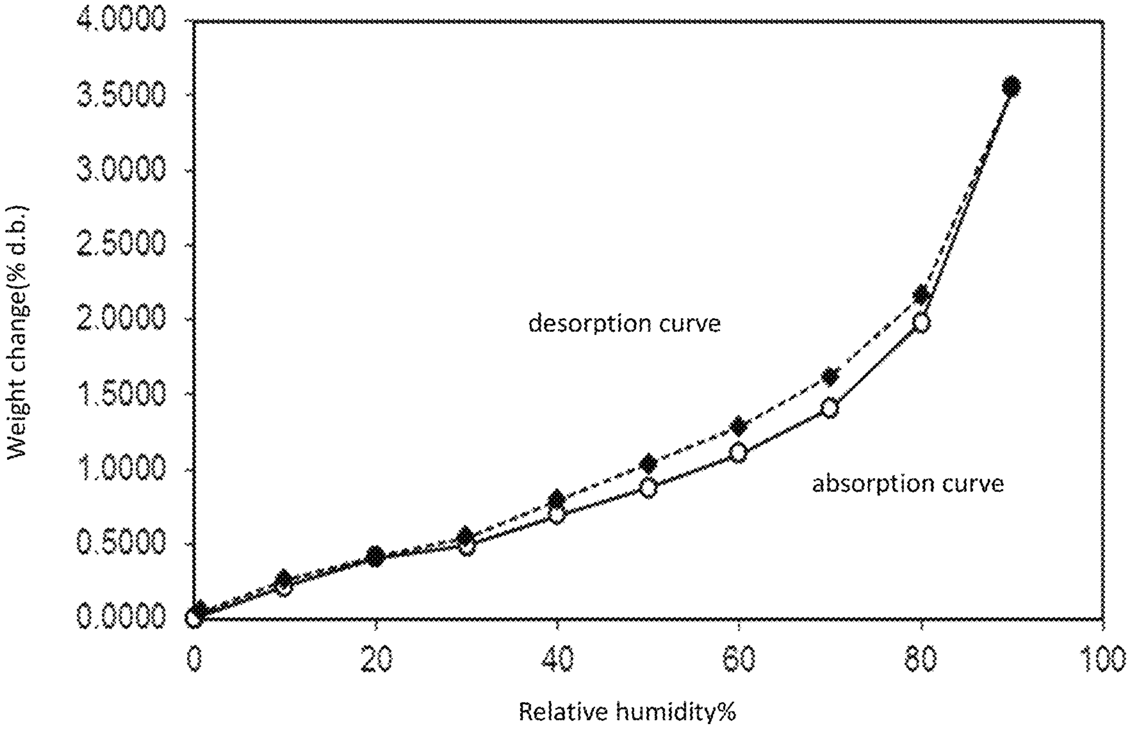
FIG. 9 is a DVS pattern of polymorphic Form I.

The X-ray powder diffraction spectra of the polymorphic Form I prepared in acetone are shown as curve 1 in FIG. 6, the peak table is shown in Table 1, and the PLM, TGA, DSC and DVS patterns are shown in FIGS. 7-9.

TGA results show that polymorphic Form I lost about 0.34% weight before 230° C. (FIG. 8); DSC has a Endothermic peak with a shoulder peak, the initial temperature is 251.55° C., and the peak value is 253.96; The peak temperature of the shoulder peak is 241.7° C. (FIG. 8). DVS shows that polymorphic Form I absorbs moisture <2% at 80% RH (FIG. 9), and the polymorph of the sample does not change before and after moisture absorption.

TABLE 1

| 2θ value | Relative intensity % | Intensity | d-value |
|---|---|---|---|
| 4.234 | 61.1 | 1000 | 20.85055 |
| 8.505 | 17.9 | 293 | 10.38828 |
| 8.96 | 24.9 | 407 | 9.86138 |
| 10.05 | 11.2 | 183 | 8.79394 |
| 11.177 | 29.9 | 489 | 7.91003 |
| 12.892 | 19.1 | 313 | 6.86121 |
| 16.438 | 13.5 | 221 | 5.3882 |
| 17.093 | 12.6 | 206 | 5.18331 |
| 18.05 | 100 | 1637 | 4.91053 |
| 18.851 | 7.1 | 116 | 4.70357 |
| 19.229 | 11.2 | 184 | 4.61209 |

TABLE 1-continued

| 2θ value | Relative intensity % | Intensity | d-value |
|---|---|---|---|
| 19.406 | 8.7 | 143 | 4.57034 |
| 20.259 | 11.4 | 187 | 4.37986 |
| 21.544 | 15.3 | 251 | 4.12148 |
| 22 | 8 | 131 | 4.03707 |
| 22.543 | 9.8 | 161 | 3.94106 |
| 23.333 | 15.7 | 257 | 3.80935 |
| 24.285 | 7.9 | 129 | 3.66203 |
| 25.613 | 10.8 | 177 | 3.47514 |
| 26.051 | 12.9 | 211 | 3.41776 |
| 26.774 | 5.8 | 95 | 3.32701 |
| 27.331 | 4.8 | 79 | 3.26048 |
| 28.441 | 8.6 | 140 | 3.13569 |
| 29.04 | 6 | 98 | 3.07233 |
| 29.529 | 8.6 | 140 | 3.02259 |
| 30.185 | 4.7 | 77 | 2.95839 |
| 33.196 | 5.1 | 83 | 2.69658 |
| 34.049 | 6 | 99 | 2.63097 |
| 34.714 | 5.3 | 86 | 2.5821 |
| 36.109 | 5.8 | 95 | 2.48549 |
| 37.076 | 6.4 | 104 | 2.42284 |
| 38.936 | 6.9 | 113 | 2.31129 |

Example 4

Room Temperature Suspension Stirring Screening

In different solvents, 20 samples were obtained by room temperature suspension stirring preparation, the results are shown in Table 2 and FIG. 10, wherein the solvent volume ratio represents mass volume ratio (g/mL) of the initial raw material and solvent, similarly hereinafter.

TABLE 2

| Results of Suspension Stirring at Room Temperature | | |
|---|---|---|
| Solvent | solvent volume ratio | Results |
| MeOH | 24.5 | Polymorphic Form I |
| EtOH | 27.2 | Polymorphic Form II |
| IPA | 27.9 | Polymorphic Form I |
| Isobutanol | 30.9 | Polymorphic Form I |
| 2-butanone | 23.9 | Polymorphic Form I |
| THF | 7.5 | clear |
| ACN | 29.9 | Polymorphic Form I |
| MTBE | 25.4 | Polymorphic Form I |
| water | 23.5 | Polymorphic Form I |
| EA | 26.2 | Polymorphic Form I |
| Acetone | 27 | Polymorphic Form I |
| IPrOAc | 24.5 | Polymorphic Form I |
| DCM | 24.5 | Polymorphic Form I |
| n-heptane | 26.2 | Polymorphic Form I |
| 1,4-dioxane | 11.6 | Polymorphic Form I |
| Butyl acetate | 24.3 | Polymorphic Form I |
| 4-Methyl-2-pentanone | 27.6 | Polymorphic Form I |
| toluene | 25 | Polymorphic Form I |
| MeOH/Water (1:1) | 24.2 | Polymorphic Form I |
| Acetone/water (1:1) | 24.6 | Polymorphic Form I |
| THF/Water (1:4) | 21.5 | Polymorphic Form I |

Figure 10:
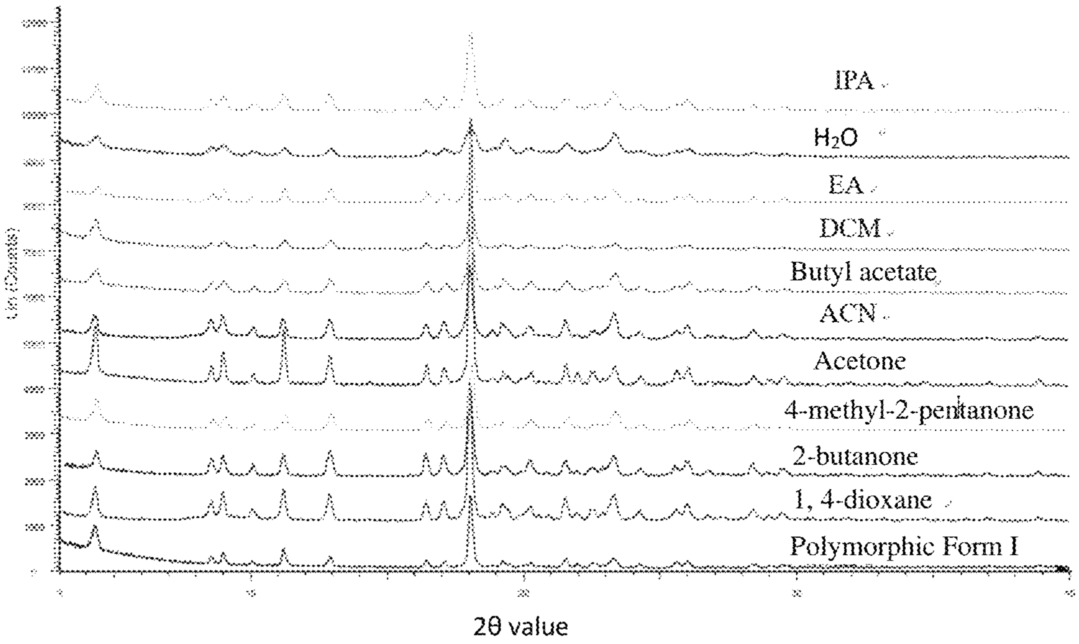
FIG. 10 is an X-ray powder diffraction pattern of the sample prepared by room temperature suspension stirring.
Figure 10:
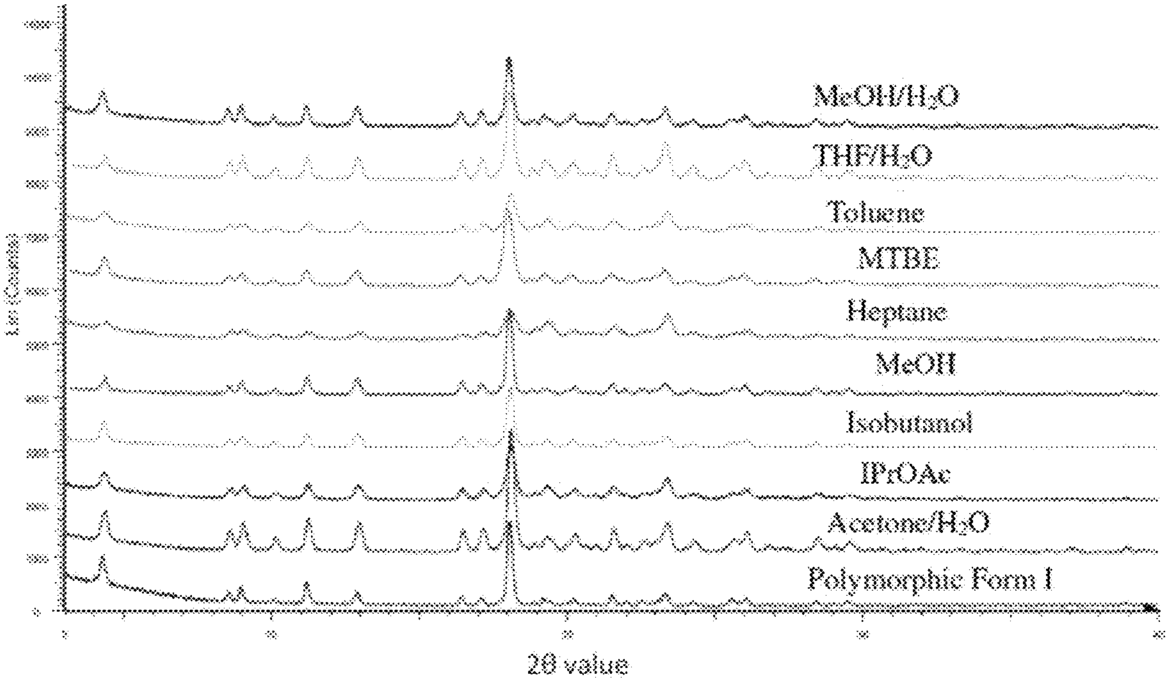
Figure 11:
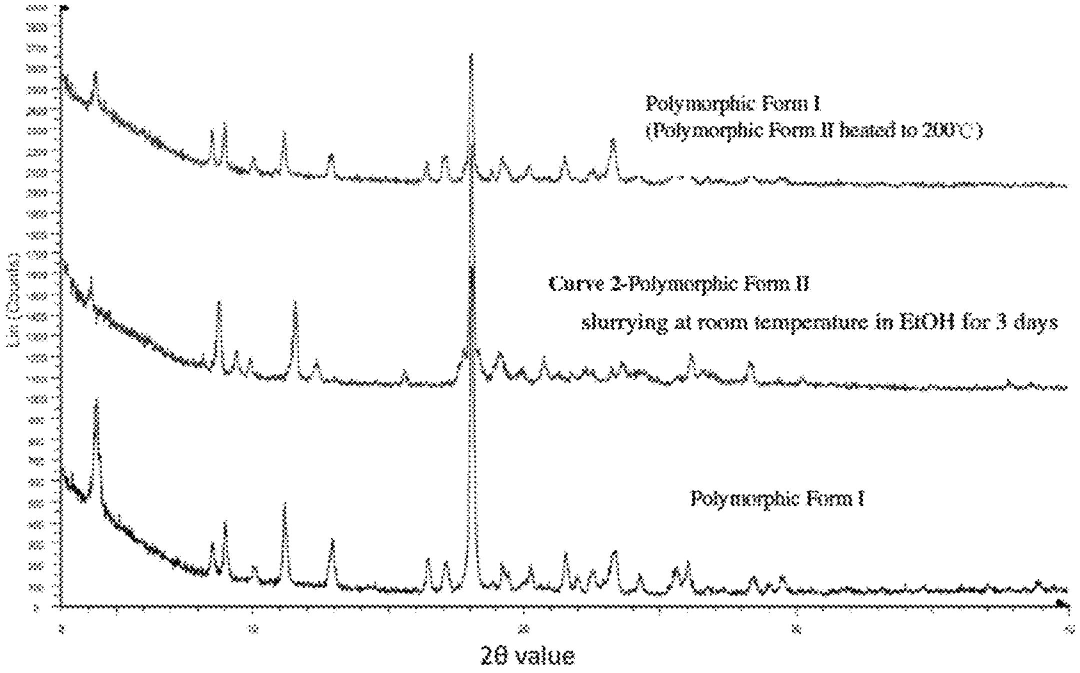
FIG. 11 is an X-ray powder diffraction pattern of polymorphic Form II.

It can be seen from FIG. 10 that most of the polymorphic From of this experiment were polymorphic Form I, but when the solvent is EtOH, the polymorphic form obtained was different from polymorphic Form I (FIG. 11), named polymorphic Form II.

Figure 12:
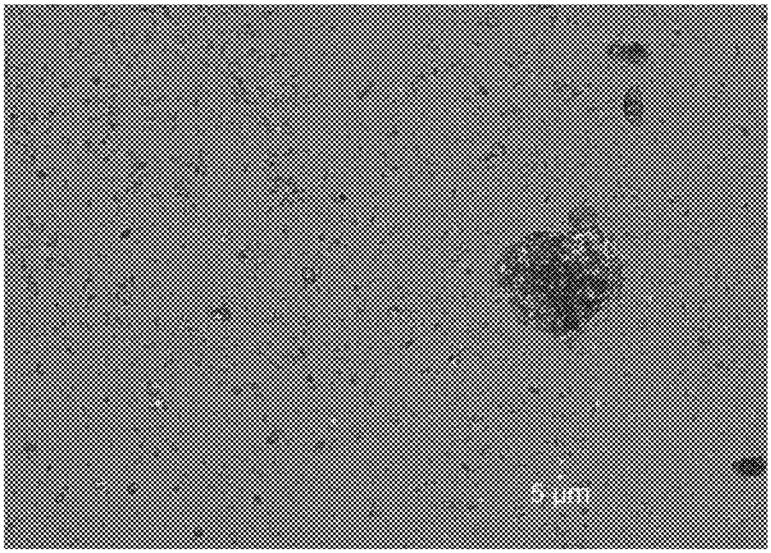
FIG. 12 is a polarizing microscope analysis photograph of polymorphic Form II.
Figure 13:
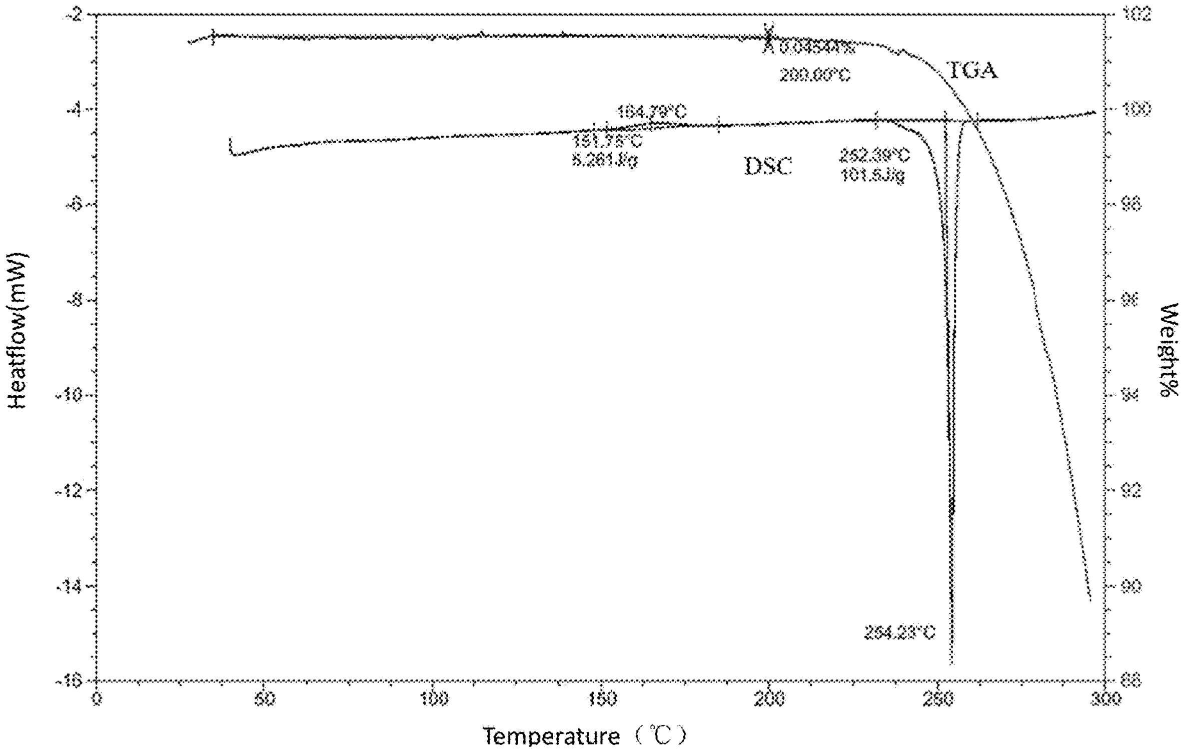
FIG. 13 is a TGA-DSC pattern of polymorphic Form II.

Polymorphic From II was characterized by PLM, TGA and DSC (FIGS. 12-13).

The results of PLM (FIG. 11) showed that the crystal particles of polymorphic Form II are small and have good dispersibility.

TGA (FIG. 12) showed that polymorphic Form II has only about 0.045% weight loss before 200° C.; It showed that polymorphic Form II was an anhydrous polymorphic Form; $^1$H NMR spectrum shows that there is no EtOH residue in the sample.

DSC (FIG. 12) has an endothermic peak and an exothermic peak, and the initial temperatures are 252.39° C. (melting point of polymorphic Form I) and 151.75° C., respectively.

Further, XRPD characterization was carried out after polymorphic Form II was heated to 200° C. The result sees FIG. 11, it can be seen that polymorphic Form II was transformed into polymorphic Form I after heating to 200° C.

The X-ray powder diffraction pattern peaks of polymorphic Form II are shown in Table 3.

TABLE 3

| 2θ value | Relative intensity % | Intensity | d-value |
|---|---|---|---|
| 4.018 | 47.4 | 584 | 21.97495 |
| 8.153 | 17.2 | 212 | 10.83558 |
| 8.722 | 38.3 | 472 | 10.13006 |
| 9.382 | 18.7 | 231 | 9.41876 |
| 9.882 | 15.9 | 196 | 8.94357 |
| 11.539 | 38.2 | 471 | 7.66263 |
| 12.333 | 14.9 | 184 | 7.17114 |
| 15.587 | 10.9 | 134 | 5.68045 |
| 17.732 | 19.6 | 242 | 4.99788 |
| 18.038 | 100 | 1233 | 4.91372 |
| 19.13 | 18.1 | 223 | 4.63562 |
| 19.91 | 11.9 | 147 | 4.45592 |
| 20.747 | 16.3 | 201 | 4.27785 |
| 21.776 | 9.9 | 122 | 4.07802 |
| 22.263 | 10.9 | 135 | 3.98987 |
| 22.525 | 10.6 | 131 | 3.94408 |
| 23.237 | 11.7 | 144 | 3.82488 |
| 23.638 | 13.5 | 166 | 3.76079 |
| 25.64 | 9.3 | 115 | 3.4716 |
| 26.164 | 17.4 | 214 | 3.4032 |
| 26.612 | 10.6 | 131 | 3.3469 |
| 28.341 | 13.6 | 168 | 3.14649 |
| 30.248 | 8.2 | 101 | 2.95238 |
| 37.843 | 7.1 | 88 | 2.37546 |

Example 5

50° C. Suspension and Stirring Screening

A certain amount of compound I sample was added to different solvents as shown in Table 4 to prepare the suspension. The suspension was stirred and slurried at 50° C. After filtration, XRPD characterization of the resulting solids was coducted.

Figure 14:
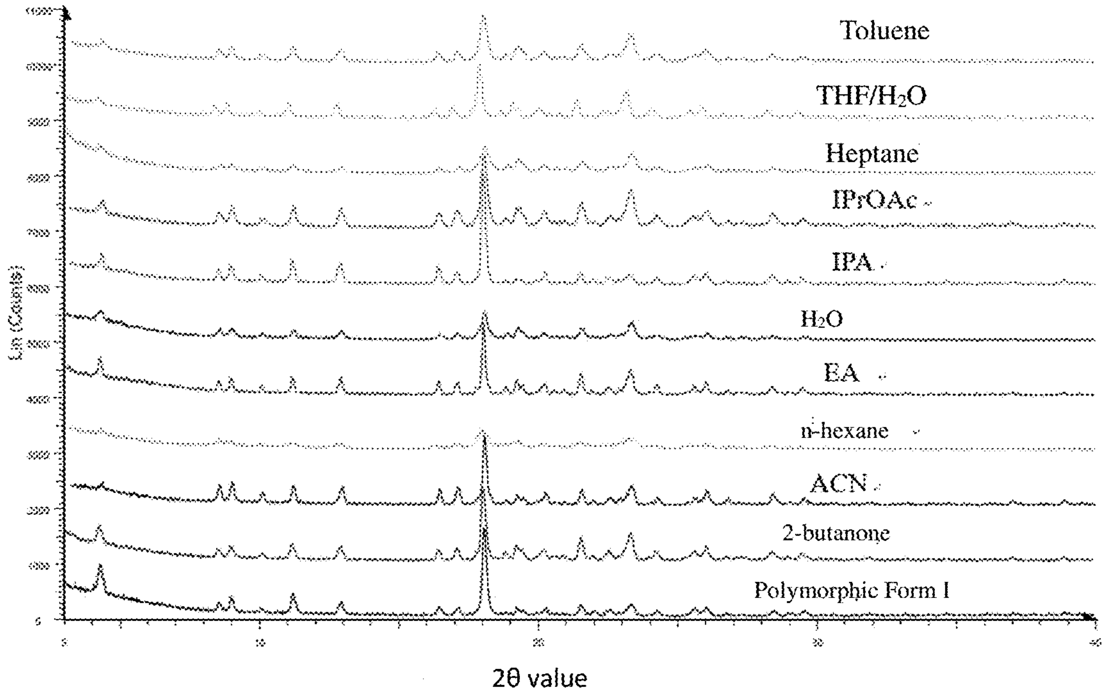
FIG. 14 is an X-ray powder diffraction pattern of the sample prepared by 50° C. suspension stirring.
Figure 15:
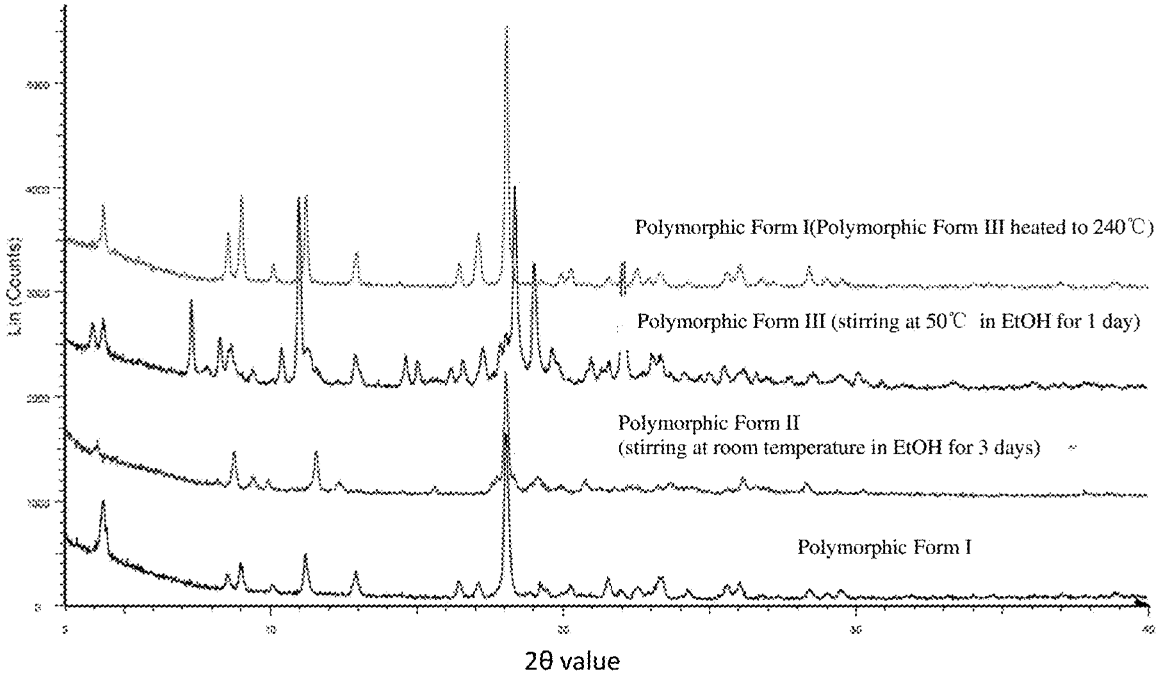
FIG. 15 is an X-ray powder diffraction pattern of polymorphic Form III.

A total of 11 samples were prepared by 50° C. suspension stirring (Table 4). Most of the samples were polymorphic Form I (FIG. 14). Only when EtOH was used as solvent, a new crystal form was obtained and named Polymorphic Form III (FIG. 15).

TABLE 4

Results of 50° C. Suspension Stirring

| Solvent | solvent volume ratio | slurrying time/day | Results |
|---|---|---|---|
| IPA | 13.0 | 2 | Polymorphic Form I |
| ACN | 14.4 | 2 | Polymorphic Form I |
| EA | 14.6 | 2 | Polymorphic Form I |
| 2-butanone | 13.0 | 2 | Polymorphic Form I |
| n-heptane | 14.5 | 2 | Polymorphic Form I |
| water | 14.2 | 2 | Polymorphic Form I |
| IPrOAc | 14.2 | 2 | Polymorphic Form I |

TABLE 4-continued

Results of 50° C. Suspension Stirring

| Solvent | solvent volume ratio | slurrying time/day | Results |
|---|---|---|---|
| Cyclohexane | 13.9 | 2 | Polymorphic Form I |
| toluene | 13.5 | 2 | Polymorphic Form I |
| THF/Water (1:4) | 13.5 | 2 | Polymorphic Form I |
| EtOH | 13.7 | 1 | Polymorphic Form III (Solvate) |

Figure 16:
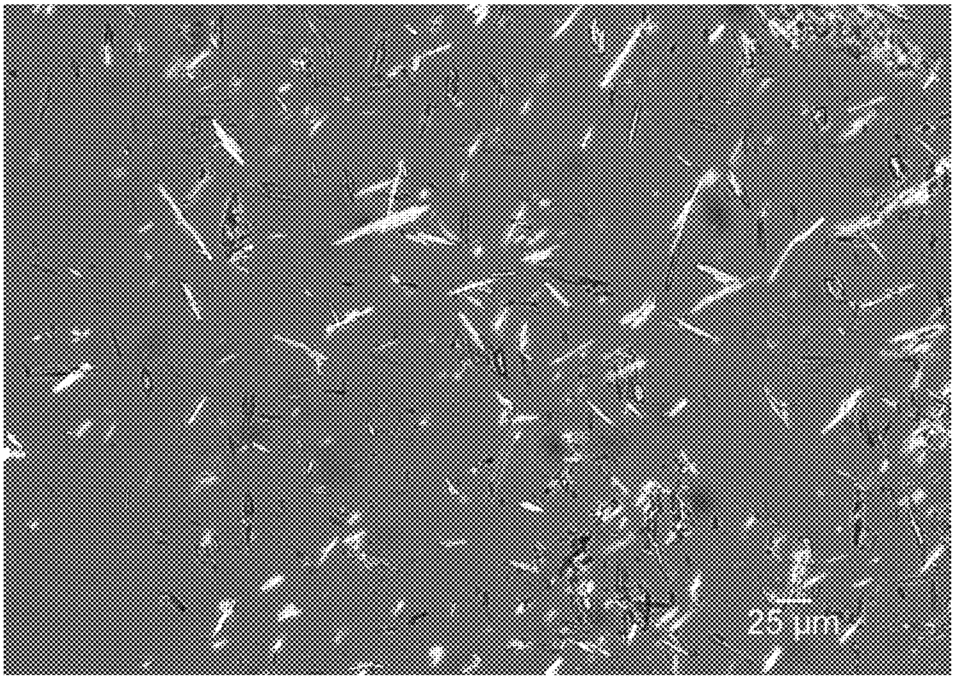
FIG. 16 is a polarizing microscope analysis photograph of polymorphic Form III.
Figure 17:
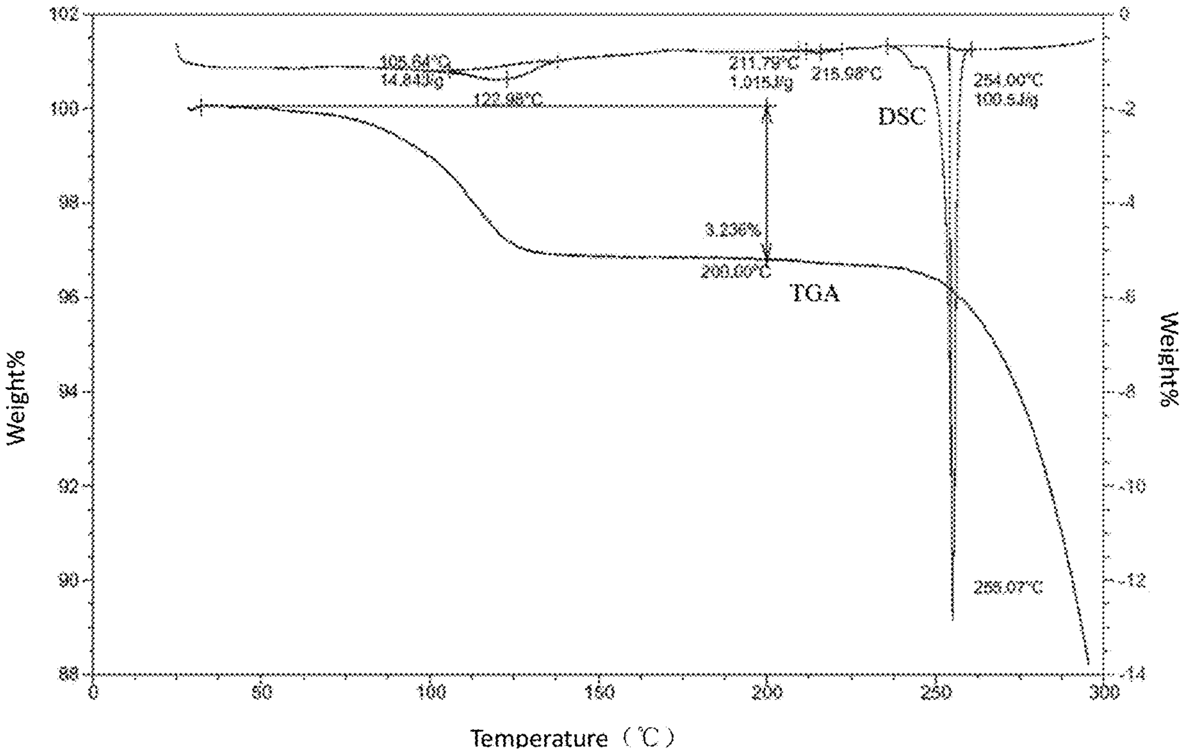
FIG. 17 is a TGA-DSC pattern of polymorphic Form III.

Polymorphic Form III was characterized by XRPD, PLM, TGA, and DSC (Figures 15-17).

PLM (FIG. 16) results showed that polymorphic Form III is a needle crystal.

TGA (FIG. 17) shows that polymorphic Form III has a weight loss of about 3.236% before 200° C., so the polymorphic Form III may be a solvent compound of EtOH (~0.3 mol); $^1$H NMR shows that there is 3.1% EtOH residue in the sample.

DSC (FIG. 17) spectrum has three endothermic peaks with initial temperatures (onset) of 105.64° C., 211.79 and 254° C., respectively.

As can be seen from FIG. 15, polymorphic Form III was heated to 240° C. and then transformed into polymorphic Form I. The exothermic peak with an initial temperature of 211.8° C. in DSC may be a crystal transformation peak.

The X-ray powder diffraction pattern of polymorphic Form III is shown in Table 5.

TABLE 5

| 2θ value | Relative intensity % | Intensity | d-value |
|---|---|---|---|
| 3.888 | 34.6 | 703 | 22.70813 |
| 4.247 | 36.7 | 745 | 20.79007 |
| 7.269 | 45.7 | 928 | 12.15182 |
| 7.773 | 14.6 | 296 | 11.36408 |
| 8.251 | 28.4 | 577 | 10.70707 |
| 8.589 | 22.5 | 457 | 10.28685 |
| 9.371 | 13.2 | 267 | 9.43044 |
| 10.352 | 23.9 | 485 | 8.53878 |
| 10.954 | 94.6 | 1920 | 8.07086 |
| 11.248 | 23.2 | 470 | 7.86049 |
| 11.587 | 13 | 264 | 7.63088 |
| 12.236 | 7.6 | 155 | 7.22746 |
| 12.887 | 20.2 | 409 | 6.86383 |
| 14.6 | 19.3 | 392 | 6.06209 |
| 15.018 | 17.2 | 348 | 5.89443 |
| 16.149 | 13.5 | 273 | 5.48399 |
| 16.561 | 17.2 | 348 | 5.3487 |
| 17.248 | 23 | 467 | 5.13714 |
| 17.855 | 25.2 | 512 | 4.9639 |
| 18.068 | 30.1 | 610 | 4.90576 |
| 18.343 | 100 | 2029 | 4.83267 |
| 19.009 | 63.1 | 1281 | 4.66491 |
| 19.605 | 22.9 | 464 | 4.52439 |
| 20.946 | 18.2 | 370 | 4.2378 |
| 21.334 | 13.1 | 266 | 4.16148 |
| 21.546 | 16.8 | 340 | 4.12107 |
| 22.04 | 79 | 1602 | 4.02983 |
| 22.708 | 11.9 | 241 | 3.91279 |
| 23.059 | 19.4 | 393 | 3.85389 |
| 23.332 | 19.5 | 396 | 3.80946 |
| 23.668 | 11.7 | 238 | 3.75609 |
| 24.139 | 11.1 | 225 | 3.68393 |
| 24.685 | 10.1 | 205 | 3.60368 |
| 25.013 | 11 | 223 | 3.55708 |
| 25.51 | 14.8 | 301 | 3.48894 |
| 26.024 | 11.4 | 231 | 3.42121 |
| 26.174 | 13.2 | 267 | 3.40189 |
| 26.592 | 10.6 | 216 | 3.34935 |
| 26.995 | 9.3 | 188 | 3.30033 |
| 27.742 | 9.2 | 186 | 3.21306 |

TABLE 5-continued

| 2θ value | Relative intensity % | Intensity | d-value |
|---|---|---|---|
| 28.518 | 9.9 | 201 | 3.1274 |
| 29.472 | 10.3 | 210 | 3.02835 |
| 30.098 | 11.2 | 228 | 2.96675 |
| 30.901 | 7.7 | 156 | 2.89147 |
| 33.326 | 7.1 | 144 | 2.68639 |
| 36.094 | 7 | 143 | 2.48644 |
| 36.8 | 5.9 | 120 | 2.44036 |
| 37.147 | 6.2 | 126 | 2.41834 |
| 37.881 | 6.7 | 135 | 2.3732 |
| 38.716 | 5 | 102 | 2.32391 |

Example 6

Screening by Cooling Crystallization

The initial raw material of Compound I was dissolved in a solvent under the stirring condition of 50° C., and then the solution was filtered (undissolved solids were separated to obtain a saturated solution of Compound I) and slowly reduced to room temperature. The obtained solid sample was filtered and then determined by XRPD.

Figure 18:
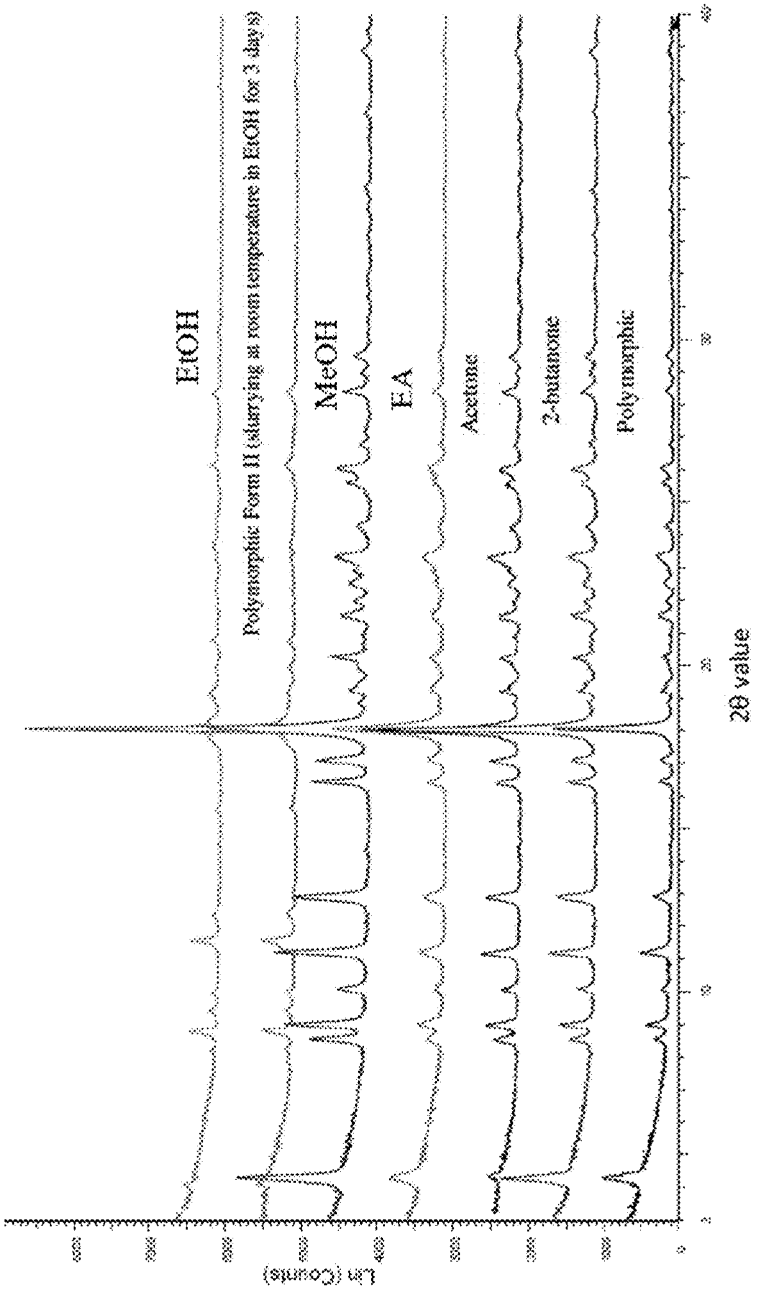
FIG. 18 is the X-ray powder diffraction pattern of the sample obtained by cooling crystallization.

A total of five samples were prepared in this experiment (Table 6), except for the polymorphic Form II obtained by cooling crystallization in EtOH, all the other samples were polymorphic Form I (FIG. 18).

TABLE 6

| Cooling Crystallization Results | | |
|---|---|---|
| Solvent | Volume ratio | Results |
| MeOH | 45.2 | Polymorphic Form I |
| EtOH | 70 | Polymorphic Form II |
| Acetone* | 57.5 | Polymorphic Form I |
| 2-butanone* | 53.8 | Polymorphic Form I |
| EA | 57.5 | Polymorphic Form I |

Note:
*indicates that there were fewer solid samples when the sample was cooled to room temperature. The sample was collected and characterized after the sample bottle was volatilized for 1 hour.

Example 7

Screening by Anti-Solvent Precipitation Method

At room temperature, an appropriate amount of compound I sample was dissolved into a certain volume of THF, MeOH, acetone and 2-butanone; the filtrate was prepared by filtration. Subsequently, under room temperature stirring conditions, different proportions of anti-solvent were gradually added. The resulting solids were filtered and subjected to an XRPD test.

Figure 19:
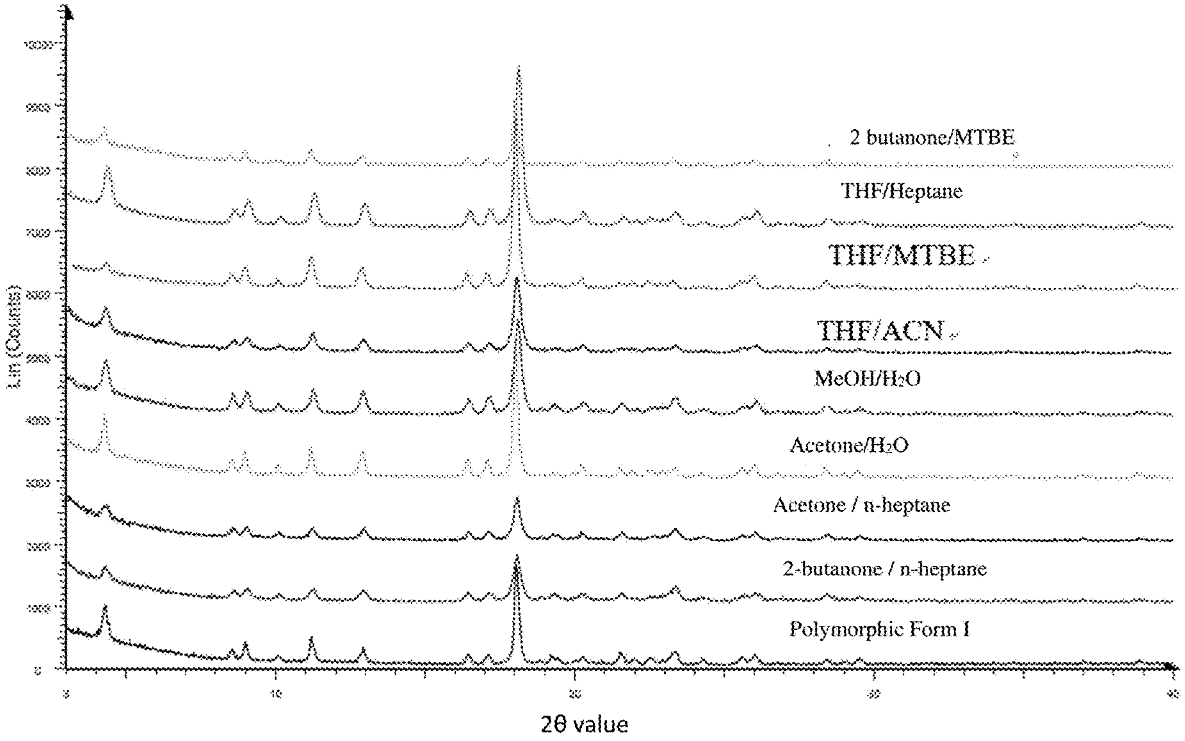
FIG. 19 is the X-ray powder diffraction pattern of the sample obtained by the counter-solvent precipitation.

A total of 17 experiments were carried out by the anti-solvent precipitation method (Table 7), and a total of 8 samples were obtained, all of which were polymorphic Form I (FIG. 19).

TABLE 7

| Results of Anti-solvent Precipitation | | | | | |
|---|---|---|---|---|---|
| Solvent | Anti-solvent | Ratio$_{(solvent/anti\text{-}solvent)}$ | solvent volume ratio | Appearance | Results |
| THF | water | 3:1 | 12 | Oils | / |
| THF | MTBE | 3:2 | 11.5 | Precipitation occurs | Polymorphic Form I |
| THF | n-heptane | 3:1 | 12.3 | Precipitation occurs | Polymorphic Form I |
| THF | ACN | 1:10 | 12.6 | Precipitation occurs | Polymorphic Form I |
| THF | EA | 1:10 | 12.2 | Small amount of precipitation | / |
| THF | IPA | 1:10 | 12.1 | clear | / |
| Acetone | water | 3:2 | 63.0 | Precipitation occurs | Polymorphic Form I |
| Acetone | MTBE | 2:3 | 150.4 | Small amount of precipitation | / |
| Acetone | n-heptane | 2:3 | 73.0 | Precipitation occurs | Polymorphic Form I |
| Acetone | EA | 1:5 | 74.1 | Small amount of precipitation | / |
| MeOH | water | 5:1 | 66.2 | Precipitation occurs | Polymorphic Form I |
| MeOH | MTBE | 1:2 | 64.5 | clear | / |
| MeOH | ACN | 1:5 | 69.9 | clear | / |
| MeOH | EA | 1:6 | 64.5 | clear | / |
| 2-butanone | water | 2:1 | 53.1 | Oils | / |
| 2-butanone | MTBE | 1:3 | 65.4 | Precipitation occurs | Polymorphic Form I |
| 2-butanone | n-heptane | 5:4 | 66.7 | Precipitation occurs | Polymorphic Form I |

Note:
/indicates that there were no solid samples or too few samples for XRPD characterization.

Example 8

Volatilization Screening

Single solvent volatilization: an appropriate amount of initial raw materials of compound I was dissolved in the solvents shown in 1-6 in Table 8 to prepare a solution with a concentration of 8 to 20 mg/mL. The obtained solution was filtered, the filtrate was volatilized at room temperature, and the obtained solid was characterized by XRPD.

Binary solvent volatilization: an appropriate amount of initial raw materials of compound I was dissolved in the solvents shown in 7-25 of Table 8 to prepare a solution with a concentration of 10 mg/mL. After filtration, the resulting filtrate was then mixed with solvent −2; then volatilized at room temperature. A total of 19 solvent systems were used to carry out the volatilization experiment of binary solvent, and the obtained solid was characterized by XRPD.

TABLE 8

Volatilization experiment results

| No. | Solvent −1 | Solvent −2 | $V_{(S-1/S-2)}$ | Results |
|---|---|---|---|---|
| 1 | MeOH | / | / | Polymorphic Form IV |
| 2 | Acetone | / | / | Polymorphic Form I |
| 3* | THF | / | / | New Spectrum Figure 1, Degradation |
| 4 | 2-butanone | / | / | Polymorphic Form I |
| 5 | 1,4-dioxane | / | / | Polymorphic Form I |
| 6 | EtOH | / | / | Polymorphic Form V |
| 7 | MeOH | EtOH | 1:1 | Polymorphic Form V |
| 8 | MeOH | Acetone | 1:1 | Polymorphic Form IV + Polymorphic Form I |
| 9 | MeOH | EA | 1:1 | Polymorphic Form I |
| 10 | MeOH | THF | 1:1 | New Spectrum Figure 1 + Polymorphic Form I |
| 11 | MeOH | water | 5:1 | Polymorphic Form IV |
| 12 | MeOH | DCM | 1:1 | Polymorphic Form IV + Polymorphic Form I |
| 13 | MeOH | ACN | 1:1 | Polymorphic Form I |
| 14 | Acetone | water | 5:2 | Polymorphic Form I |
| 15* | Acetone | THF | 1:1 | New Spectrum Figure 1, Degradation |
| 16 | Acetone | EA | 1:1 | Polymorphic Form I |
| 17 | Acetone | 2-butanone | 1:1 | Polymorphic Form I |
| 18 | Acetone | DCM | 1:1 | Polymorphic Form I |
| 19 | Acetone | ACN | 1:1 | Polymorphic Form I |
| 20 | THF | EA | 1:1 | Polymorphic Form I |
| 21 | THF | MTBE | 1:1 | Polymorphic Form I |
| 22 | THF | 2-butanone | 1:1 | amorphous |
| 23* | THF | water | 1:1 | New Spectrum Figure 2 |
| 24 | THF | ACN | 1:1 | Polymorphic Form I |
| 25 | THF | DCM | 1:1 | Polymorphic Form I |

*$^1$H NMR showed degradation in the sample, and these spectra were not named. THF may have caused degradation in sample volatilization.

Figure 20:
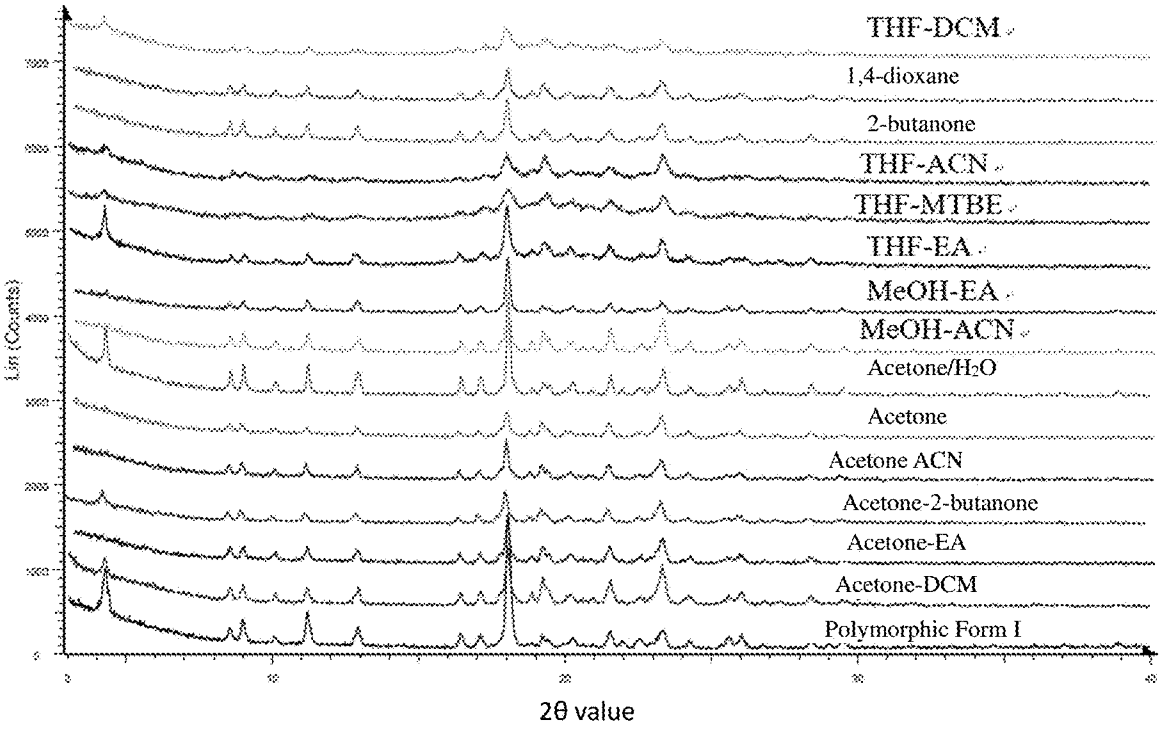
FIG. 20 is the X-ray powder diffraction pattern of the sample obtained by the volatile method.
Figure 20:
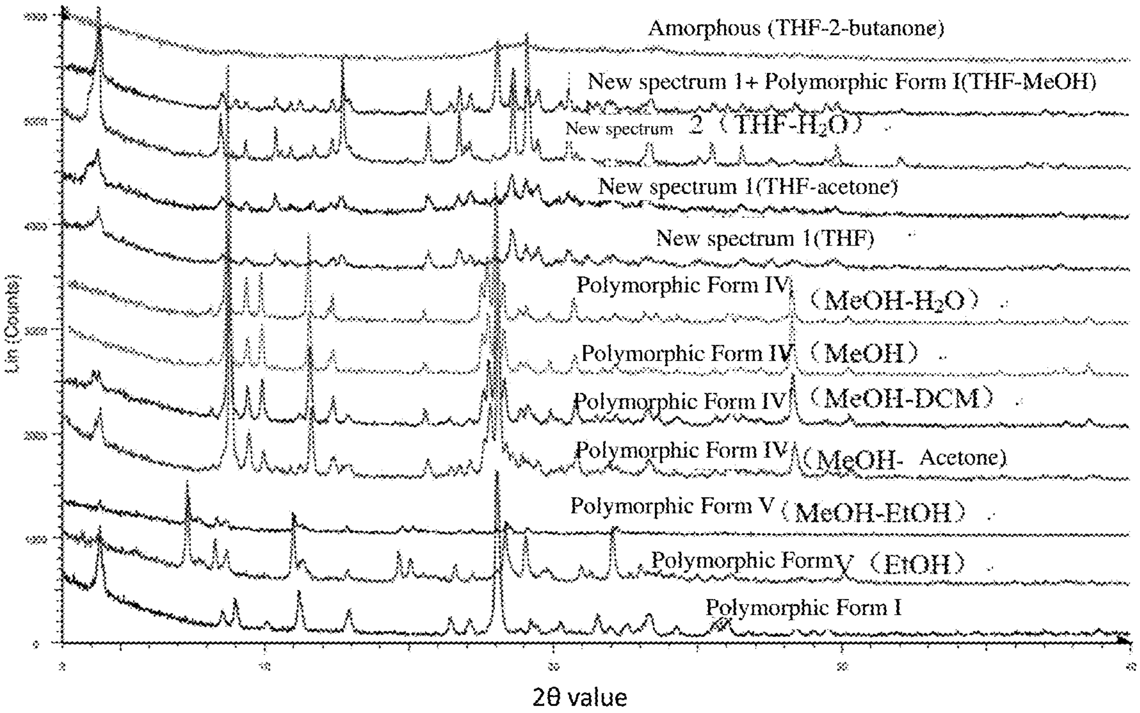

As shown in Table 8, 25 samples were obtained by the volatilization method. The XRPD spectrum was shown in FIG. 20.

The XRPD pattern of the sample obtained by volatilization in THF, MeOH-THF, THF-water, MeOH, MeOH-water and MeOH-EtOH (FIG. 20) is different from the above known polymorphic pattern.

$^1$H NMR showed that the samples in THF, MeOH-THF and THF-water were degraded, which may be caused by THF in volatilization, so these spectra were not named.

Samples volatilized in MeOH and MeOH-water have the same crystal form and are named polymorphic Form IV. The sample volatilized in MeOH-DCM is a mixture of polymorphic Form IV and polymorphic Form I.

Figure 21:
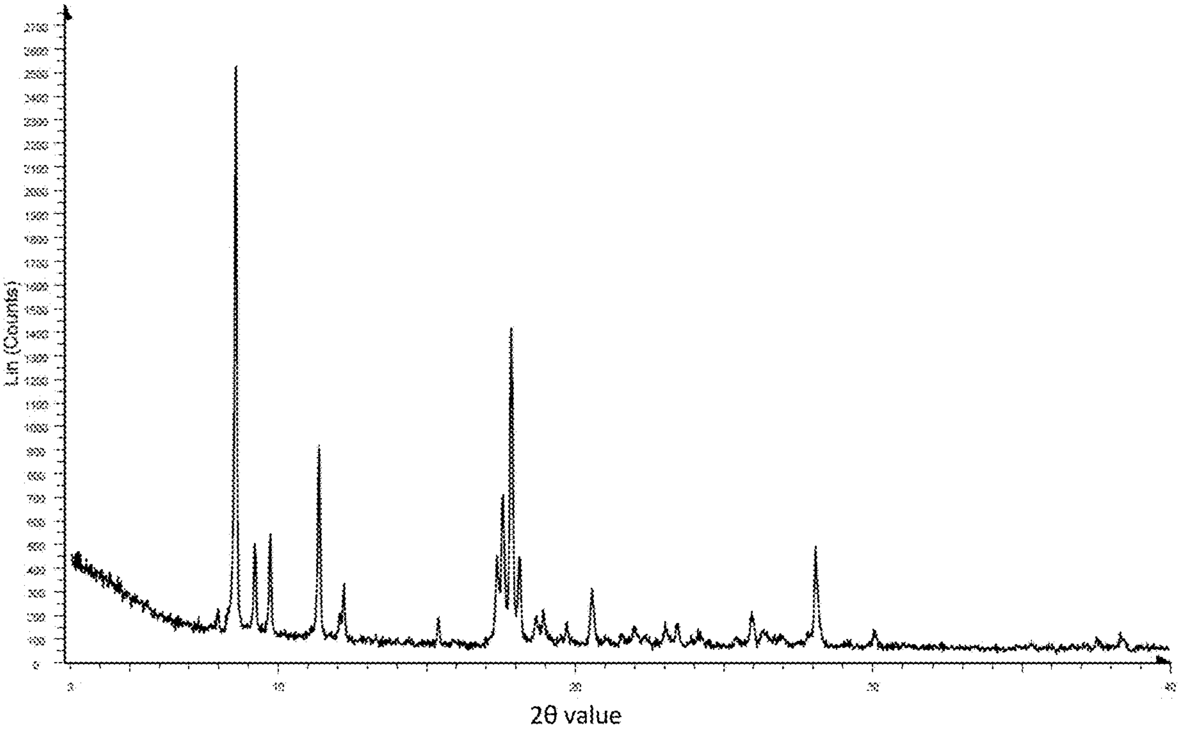
FIG. 21 is an X-ray powder diffraction pattern of polymorphic Form IV.
Figure 22:
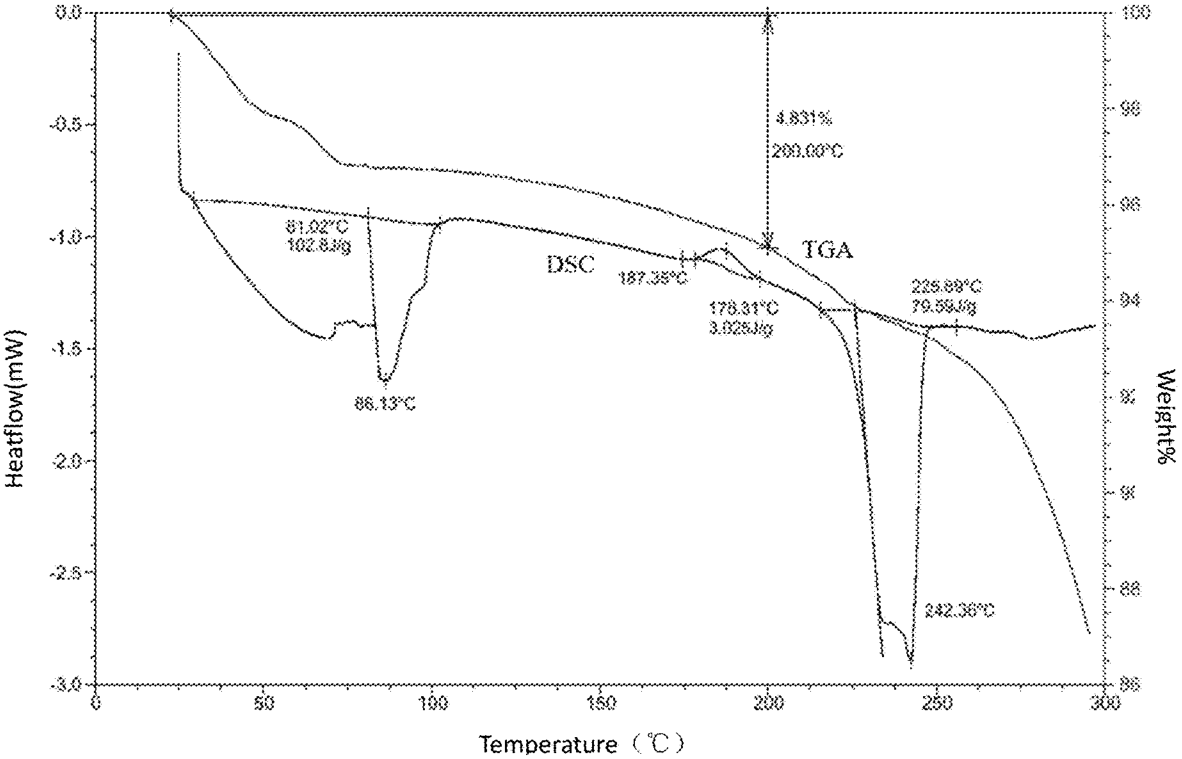
FIG. 22 is a TGA-DSC pattern of polymorphic Form IV.

Polymorphic Form IV was characterized by XRPD, TGA, and DSC (FIGS. 21-22).

TGA spectrum (FIG. 22) showed that polymorphic Form IV had a weight loss of ~4.83% before 200° C. $^1$H NMR showed that there was no organic solvent residue in the sample. Polymorphic Form IV may be a hydrate (~1 mole of water).

The DSC spectrum (FIG. 22) had two broad endothermic peaks and one exothermic peak. And the polymorphic Form was heated to 200° C. and then transformed into polymorphic Form I.

The X-ray powder diffraction spectrum of Polymorphic Form IV obtained in the number 1 experiment is shown in FIG. 21, and the peak table is shown in Table 9.

TABLE 9

| 2θ value | Relative intensity % | Intensity | d-value |
|---|---|---|---|
| 5.518 | 10.2 | 257 | 16.00302 |
| 7.903 | 8 | 202 | 11.17841 |
| 8.529 | 100 | 2532 | 10.35949 |
| 9.177 | 19.7 | 500 | 9.62871 |
| 9.696 | 21.3 | 539 | 9.11499 |
| 11.324 | 36 | 912 | 7.80772 |
| 12.152 | 12.8 | 325 | 7.27731 |
| 14.32 | 3.6 | 90 | 6.18027 |
| 15.359 | 7.2 | 182 | 5.76433 |
| 17.338 | 17.5 | 444 | 5.11053 |
| 17.556 | 28 | 708 | 5.04767 |
| 17.824 | 56.2 | 1423 | 4.97225 |
| 18.085 | 17.4 | 441 | 4.90115 |
| 18.665 | 7.5 | 190 | 4.7501 |
| 18.909 | 8.6 | 217 | 4.68947 |
| 19.684 | 6.4 | 163 | 4.50657 |
| 20.547 | 12.1 | 306 | 4.31914 |
| 21.038 | 3.7 | 93 | 4.21936 |
| 21.565 | 4.5 | 114 | 4.11742 |
| 21.974 | 5.8 | 147 | 4.0417 |
| 22.297 | 4.1 | 104 | 3.98383 |
| 23.006 | 6.4 | 162 | 3.86268 |
| 23.425 | 6.3 | 159 | 3.79461 |
| 24.161 | 4.8 | 121 | 3.68063 |
| 25.413 | 3.6 | 92 | 3.50211 |
| 25.955 | 8.1 | 205 | 3.43016 |
| 26.328 | 5.3 | 133 | 3.38232 |
| 26.945 | 4.3 | 108 | 3.30626 |
| 28.107 | 19.4 | 491 | 3.17218 |
| 30.093 | 5 | 127 | 2.96727 |
| 35.358 | 3.3 | 83 | 2.53653 |
| 37.243 | 3.1 | 79 | 2.41233 |
| 37.615 | 3.4 | 87 | 2.38932 |
| 38.42 | 4.2 | 107 | 2.34109 |

The sample obtained by volatilization in EtOH and MeOH-EtOH was a new crystal form, named polymorphic Form V.

The polymorphic Form V was characterized by XRPD, TGA and DSC.

TGA spectrum (FIG. 24) showed that the sample had 8.64% weight loss before 200° C. $^1$H NMR showed that there were 5.2% EtOH (~0.5 mol) and 0.51% MeOH residues in the sample. Polymorphic Form V may be a solvent compound of mixed solvent.

DSC spectrum (FIG. 24) has three endothermic peaks with initial temperatures of 59.19° C., 103.16° C. and 237.82° C., respectively. It can be seen from FIG. 23 that the polymorphic Form V was heated to 200° C. and then converted into the polymorphic Form I.

Figure 23:
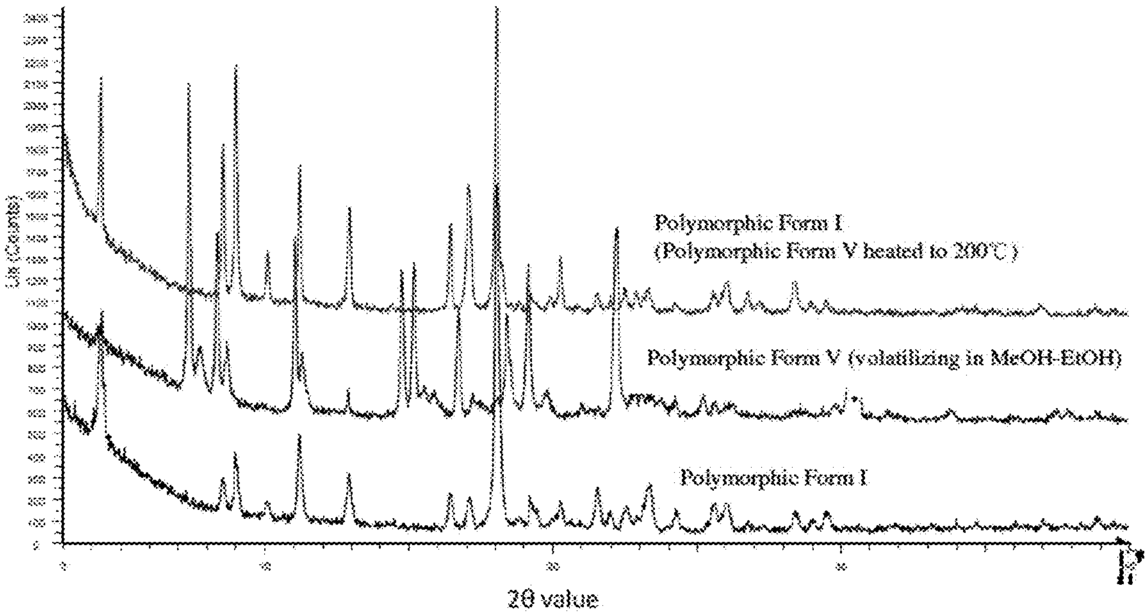
FIG. 23 is an X-ray powder diffraction pattern of polymorphic Form V.

The X-ray powder diffraction spectrum of the polymorphic Form V obtained in the number 7 experiment was shown in FIG. 23, and the peak table was shown in Table 10.

TABLE 10

| 2θ value | Relative intensity % | Intensity | d-value |
|---|---|---|---|
| 4.248 | 30.2 | 482 | 20.78529 |
| 7.335 | 100 | 1598 | 12.04268 |
| 7.712 | 25 | 399 | 11.45466 |
| 8.304 | 57.4 | 917 | 10.63906 |
| 8.643 | 26.3 | 421 | 10.22307 |
| 11.01 | 56.1 | 897 | 8.02981 |
| 11.272 | 22.7 | 363 | 7.84349 |
| 12.843 | 12.5 | 200 | 6.88747 |
| 14.733 | 46.7 | 747 | 6.00793 |
| 15.132 | 48.6 | 776 | 5.85043 |
| 15.529 | 13 | 208 | 5.70179 |
| 15.839 | 10.8 | 172 | 5.59077 |
| 16.712 | 35.4 | 565 | 5.30065 |
| 17.201 | 11 | 176 | 5.15087 |
| 18.067 | 9.9 | 159 | 4.906 |
| 18.402 | 33.9 | 541 | 4.81746 |
| 19.142 | 48.7 | 779 | 4.6329 |
| 19.748 | 11.1 | 177 | 4.49195 |
| 21.002 | 8.3 | 132 | 4.22649 |
| 21.563 | 7.4 | 119 | 4.11777 |
| 22.2 | 58.8 | 940 | 4.00106 |
| 22.824 | 11.7 | 187 | 3.89303 |
| 23.365 | 10.1 | 162 | 3.80417 |
| 23.706 | 9.1 | 146 | 3.75023 |
| 24.235 | 9.9 | 159 | 3.66949 |
| 25.202 | 10.6 | 169 | 3.53096 |
| 25.628 | 8.7 | 139 | 3.47313 |
| 26.249 | 8.1 | 129 | 3.39235 |
| 29.788 | 8 | 128 | 2.99686 |
| 30.318 | 16.8 | 268 | 2.94575 |
| 30.621 | 13.8 | 221 | 2.91725 |
| 31.654 | 6.3 | 100 | 2.82435 |
| 33.84 | 6.5 | 104 | 2.64674 |
| 37.546 | 6.8 | 108 | 2.39359 |
| 37.898 | 6.6 | 105 | 2.37217 |
| 38.907 | 6.2 | 99 | 2.31295 |

Example 9

65° C. Suspension and Stirring Screening

Since there is a shoulder peak in the melting peak of polymorphic Form I, it is suspected that there may be a higher melting point crystal form. In order to obtain this crystal form, the suspension stirring experiment of compound I at 65° C. was carried out.

A certain compound I sample was weighed, the solvent shown in Table 11 was added to prepare the suspension. The resulting suspension was stirred at 65° C. for 3 days. The resulting solid samples were filtered and collected for XRPD characterization.

TABLE 11

65° C. suspension stirring result

| Solvent | Volume ratio | 1 day results | 3 day results |
|---|---|---|---|
| ACN | 15.3 | Polymorphic Form I | Polymorphic Form I |
| IPrOAc | 14.2 | Polymorphic Form I | Polymorphic Form I |
| EA | 14.9 | Polymorphic Form I | Polymorphic Form I |
| IPA | 14.3 | Polymorphic Form I | Polymorphic Form I |
| water | 14.7 | Polymorphic Form I | Polymorphic Form I |
| toluene | 14.5 | Polymorphic Form I | Polymorphic Form I |
| DMF/$H_2O$ (1:1) | 13.9 | Polymorphic Form VI | Polymorphic Form VI |

Figure 24:
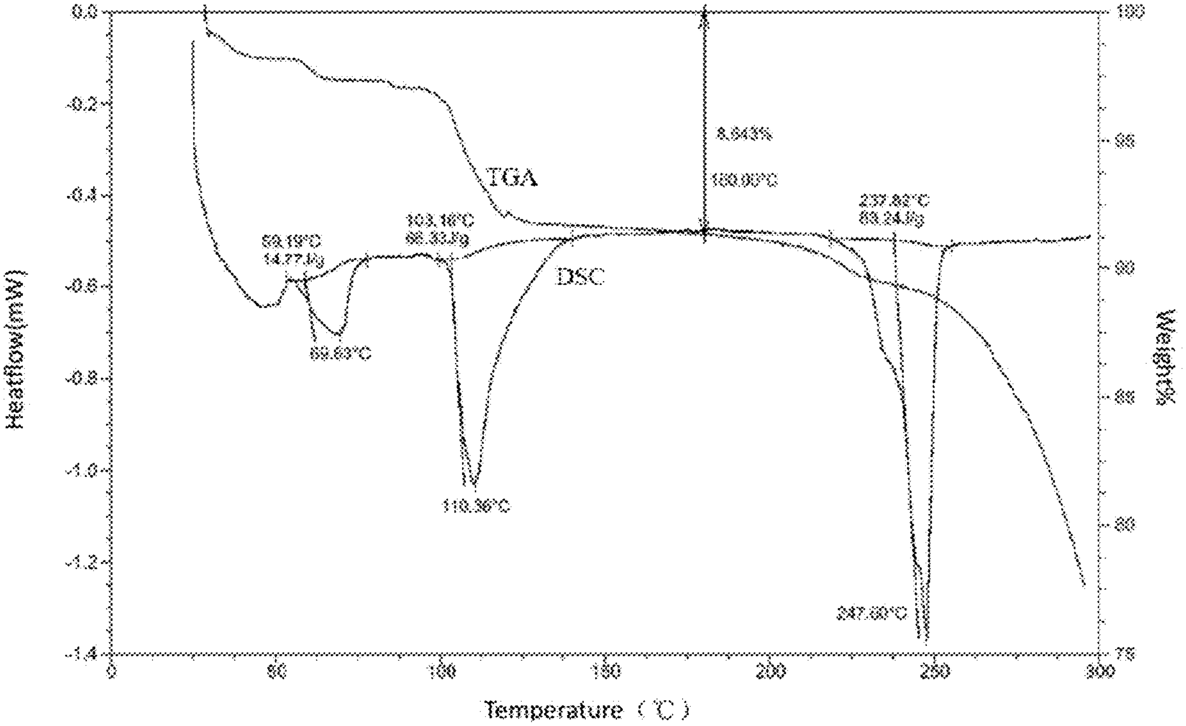
FIG. 24 is a TGA-DSC pattern of polymorphic Form V.
Figure 25:
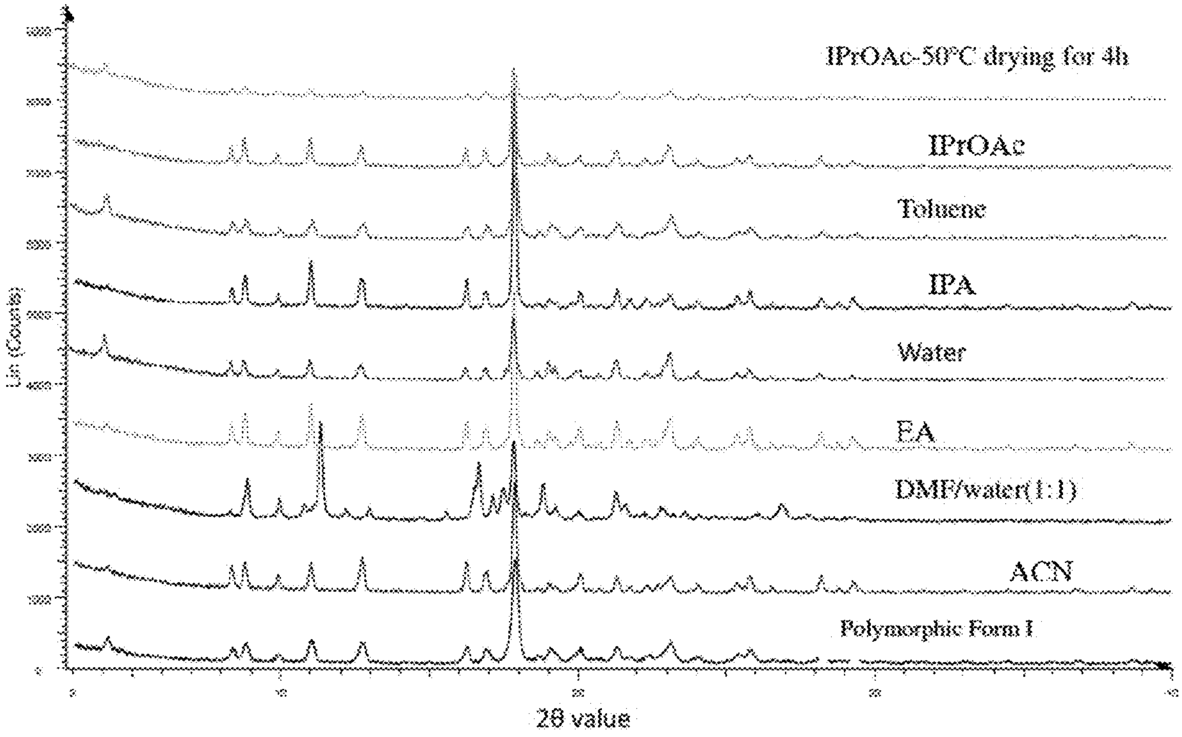
FIG. 25 is the X-ray powder diffraction pattern of the sample obtained by 65° C. suspension stirring for one day.
Figure 26:
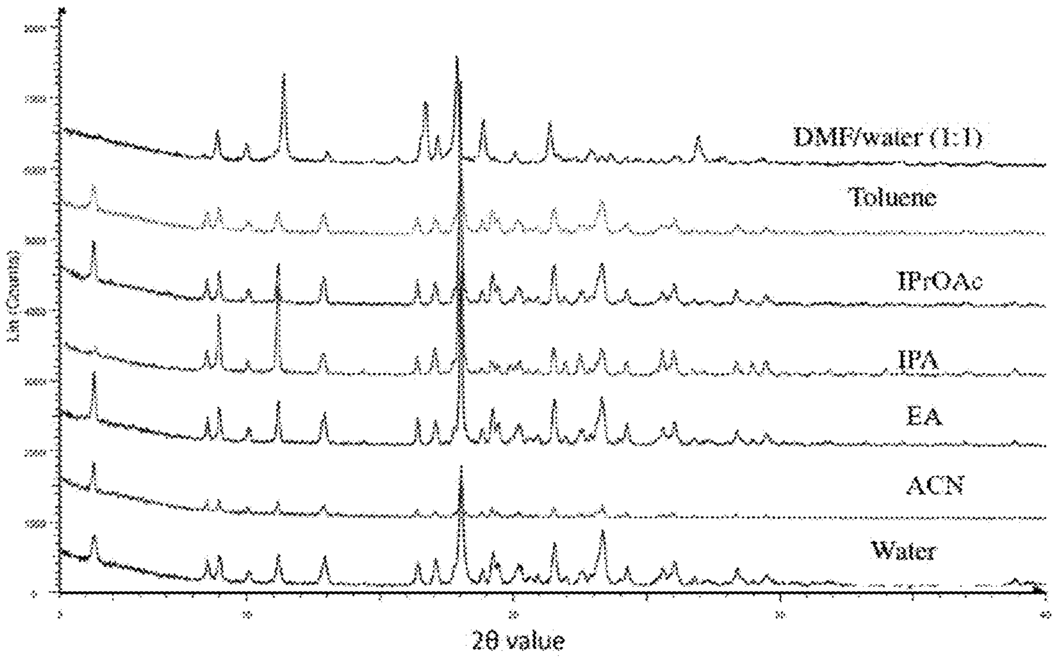
FIG. 26 is the X-ray powder diffraction pattern of the sample obtained by 65° C. suspension to crystal for 3 days.

Seven samples were prepared in this experiment (Table 11), and XRPD showed that all samples were polymorphic Form I except those obtained in DMF/water (FIGS. 23-24). The crystal form obtained in DMF/water was named Polymorphic Form VI.

Figure 27:
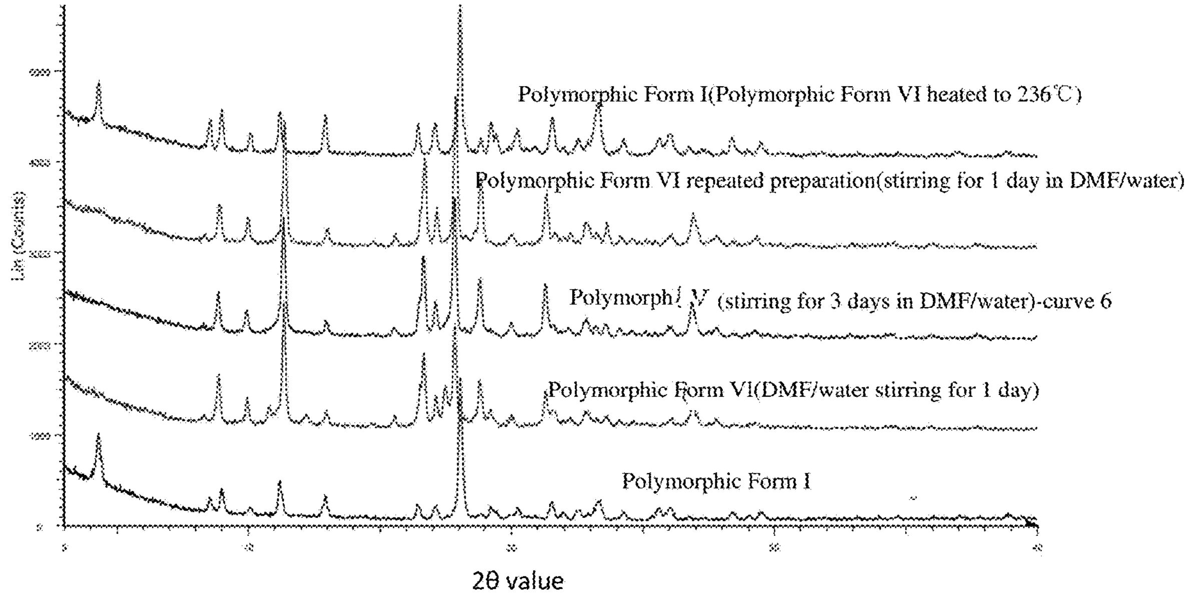
FIG. 27 is the X-ray powder diffraction pattern of polymorphic Form VI.
Figure 28:
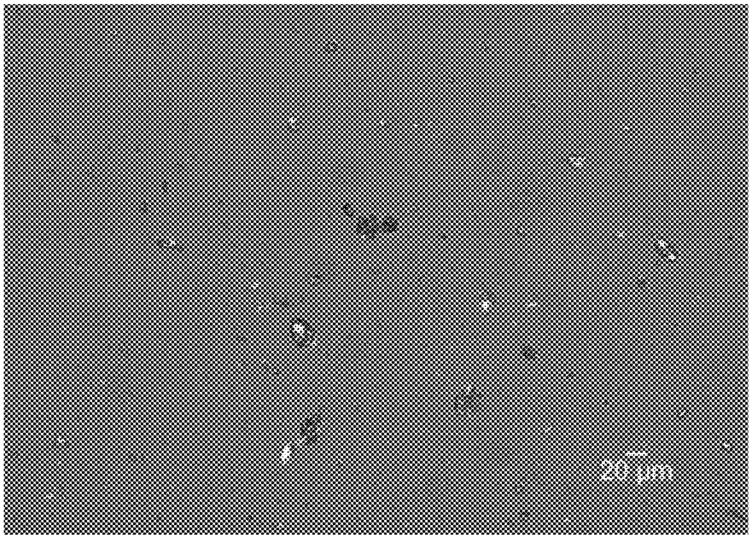
FIG. 28 is a polarizing microscope analysis photograph of polymorphic Form VI.

Polymorphic Form VI was repeatedly prepared in DMF/$H_2O$ at 65° C. and characterized by PLM, XRPD, TGA, and DSC (FIGS. 27-28).

PLM (FIG. 28) showed that polymorphic Form VI is a small particle crystal.

Figure 29:
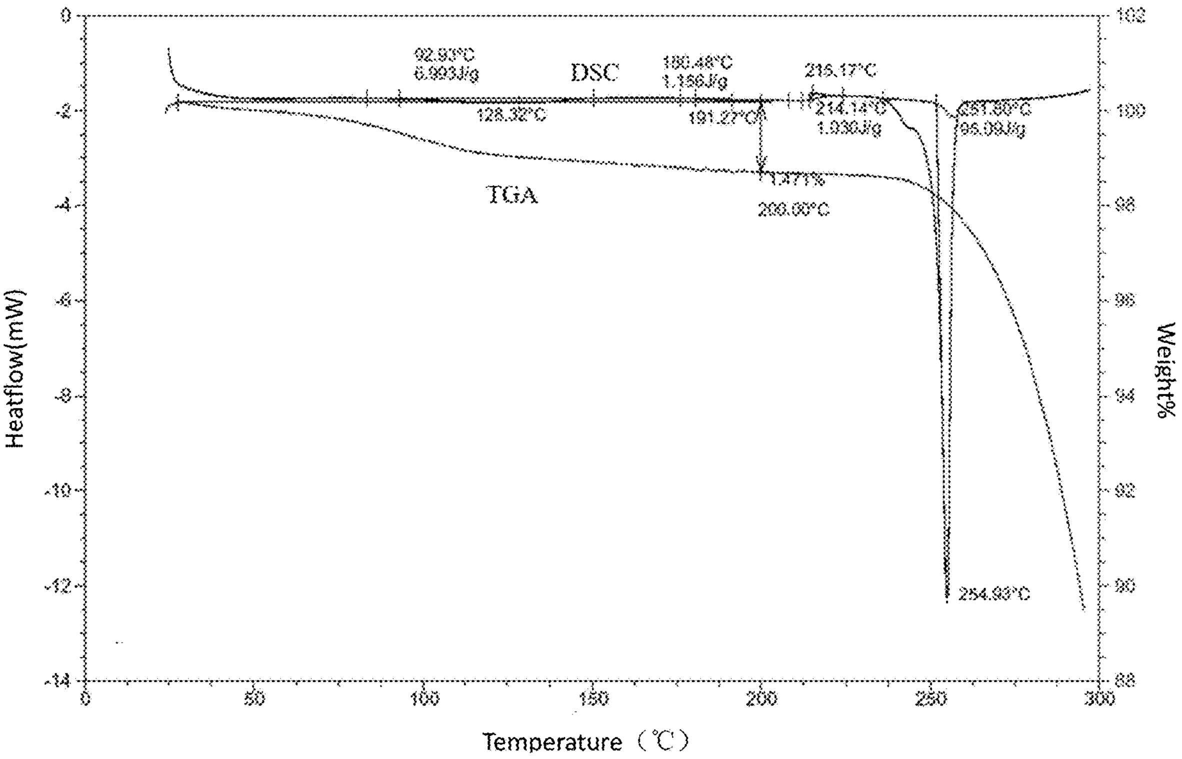
FIG. 29 is a TGA-DSC pattern of polymorphic Form VI.

TGA spectrum (FIG. 29) showed that the sample had 1.47% weight loss before 200° C. $^1$H NMR showed that there was 1.47% DMF residue in the sample, therefore, polymorphic From VI was the solvent compound of DMF (~0.1 mol).

DSC spectrum (FIG. 29) had three endothermic peaks with an initial temperature of 92.93° C., 180.48° C. and 251.80° C., in addition to an exothermic peak with an initial temperature of 215.17° C. And the crystal form was heated to about 236° C. and then transformed into polymorphic Form I (FIG. 27).

The X-ray powder diffraction spectrum of polymorphic Form VI is shown in FIG. 27, and the peak table is shown in Table 12.

TABLE 12

| 2θ value | Relative intensity % | Intensity | d-value |
|---|---|---|---|
| 8.279 | 14.9 | 218 | 10.67178 |
| 8.839 | 45 | 657 | 9.99576 |
| 9.918 | 26.9 | 393 | 8.91133 |
| 10.772 | 20.8 | 303 | 8.20627 |
| 11.326 | 100 | 1460 | 7.80624 |
| 12.172 | 16.3 | 238 | 7.26562 |
| 12.948 | 16.8 | 246 | 6.83179 |
| 14.703 | 8.4 | 122 | 6.02 |
| 15.527 | 13.1 | 191 | 5.70242 |
| 16.638 | 61.4 | 896 | 5.32402 |
| 17.11 | 28.7 | 419 | 5.17828 |
| 17.474 | 36.6 | 534 | 5.07103 |
| 17.827 | 82.9 | 1211 | 4.97159 |
| 18.226 | 13.2 | 192 | 4.86355 |
| 18.799 | 40.3 | 589 | 4.71666 |
| 19.215 | 18.7 | 273 | 4.61543 |
| 20.022 | 14.1 | 206 | 4.43108 |
| 21.306 | 33.4 | 488 | 4.16694 |
| 21.608 | 21.4 | 313 | 4.10938 |
| 22.241 | 12.4 | 181 | 3.99386 |
| 22.86 | 16.8 | 246 | 3.88698 |
| 23.236 | 11.4 | 166 | 3.82496 |
| 23.612 | 14.2 | 207 | 3.76486 |
| 24.129 | 10.8 | 157 | 3.68538 |
| 24.616 | 10.1 | 147 | 3.61361 |
| 26.07 | 12 | 175 | 3.41528 |
| 26.908 | 21 | 307 | 3.31074 |
| 27.816 | 11.1 | 162 | 3.20469 |
| 29.347 | 8.2 | 120 | 3.04097 |
| 31.328 | 5.2 | 76 | 2.85301 |
| 35.977 | 5.4 | 79 | 2.49431 |

Examples 10

DSC Heat Treatment Screening

The DSC heating-cooling-heating cycle was used to try to find a crystal form with a higher melting point.

Figure 30:
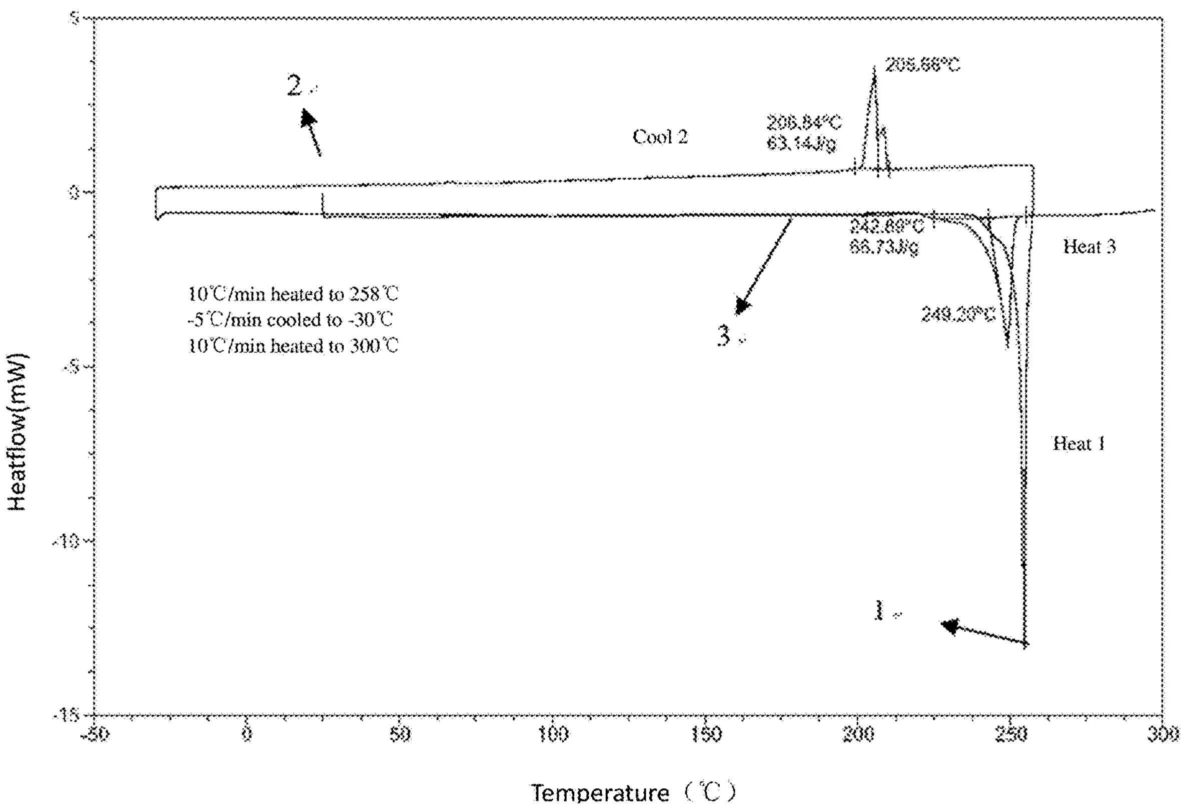
FIG. 30 is a DSC heat treatment spectrum.

The polymorphic Form I of the compound of formula I was heated from room temperature to 260° C. at the rate of 10° C./min by DSC, then cooled from 260° C. to −30° C. at the rate of −5° C./min, and finally heated from −30° C. to 300° C. at the rate of 10° C./min. The DSC spectrum is shown in FIG. 30.

During the cooling process, there is an obvious exothermic peak. The initial temperature of the exothermic peak is 206.8° C., which should be caused by crystal transformation. XRPD characterization was performed on three different positions during DSC treatment.

Figure 31:
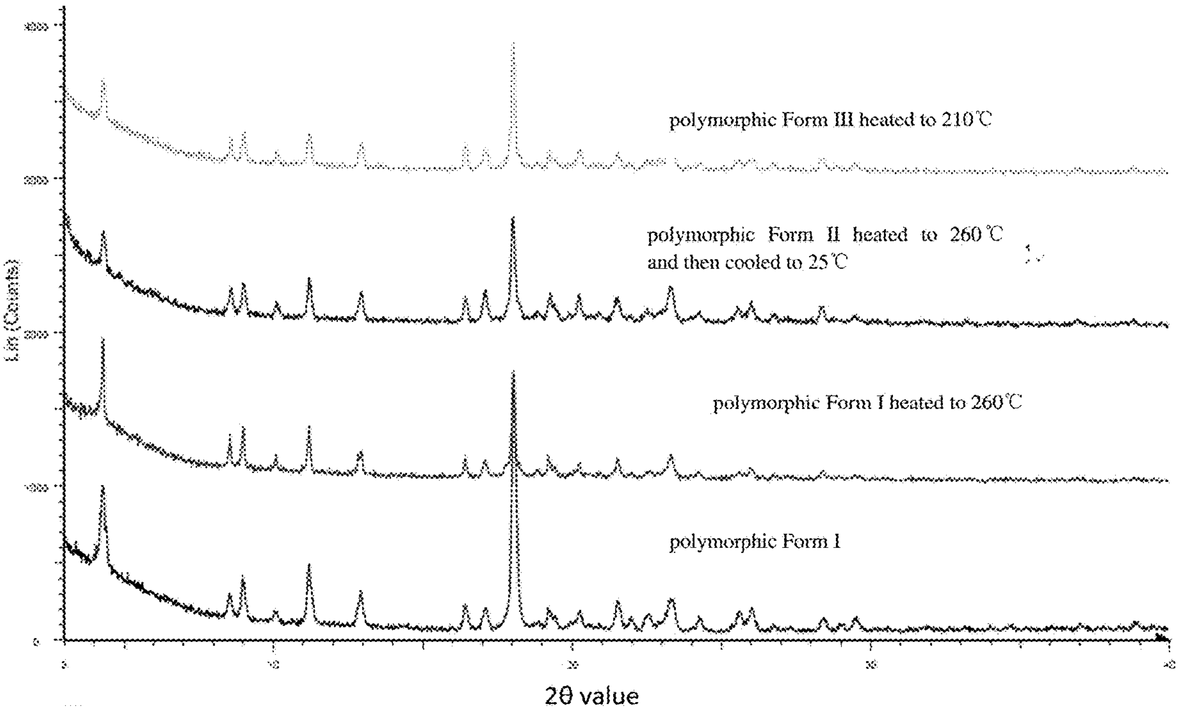
FIG. 31 is a DSC heat treatment X-ray powder diffraction spectrum.

As shown in FIG. 31, the results showed that the crystal forms of the samples are all polymorphic Form I at positions 1, 2, and 3.

Example 11

Crystal Transformation Experiment of Polymorphic Form I and Polymorphic Form II

Suspension crystal transformation experiments were carried out on Polymorph I and polymorph II at room temperature and 50° C. respectively (Table 13). The resulting solid was characterized by XRPD.

After stirring for 1 day, all samples were converted into polymorphic Form I. This showed that polymorphic Form I is a thermodynamically stable crystal form.

TABLE 13

Results of crystal transformation experiment

| Solvent | solvent volume ratio | Temperature | Results |
|---|---|---|---|
| water | 27.2 | RT | Polymorphic Form I |
| water | 27.2 | 50° C. | Polymorphic Form I |
| EtOH/Water (1:1) | 27.2 | RT | Polymorphic Form I |
| EtOH/Water (1:1) | 26.6 | 50° C. | Polymorphic Form I |

Example 12 Stability Determination of Polymorphic Form I at 25° C./92.5% RH

Figure 32:
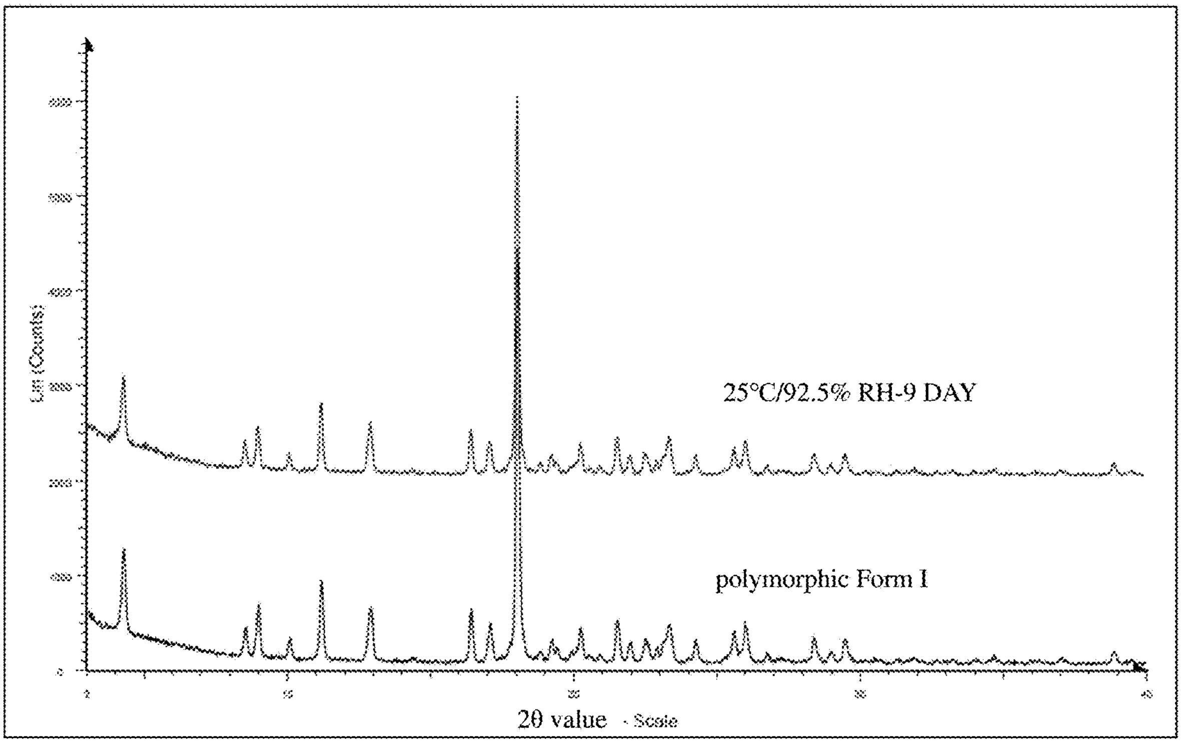
FIG. 32 is an X-ray powder diffraction pattern of polymorphic Form I in 25° C./92.5% RH environment for 9 days.

Polymorphic Form I was left at 25° C./92.5% relative humidity (RH) for 9 days. As shown in FIG. 32, XRPD shows that the polymorphic Form I can remain unchanged for a long time in a high humidity environment. This shows that polymorphic Form I has good stability in high humidity environment.

Example 13 Pharmaceutical Composition

Compound I Polymorphic Form I 20 g

Starch 140 g

Microcrystalline cellulose 60 g

According to the conventional method, after the above-mentioned substances were mixed evenly, they were loaded into ordinary gelatin capsules to obtain 1000 capsules.

In summary, the present invention provides polymorphic Form I-VI of the compound of Formula I. Polymorphic compound I has the characteristics of high purity, high stability and good solubility, and the preparation process is simple and stable, which has remarkable advantages in industrial production. Among them, polymorphic Form I and polymorphic Form II are anhydrous and solvent-free polymorphic forms. In particular, polymorphic form I is thermodynamically stable Polymorph, with stable property, non-agglomeration, easy to disperse, especially suitable for preparation process.

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A polymorph of a compound of formula I, wherein the polymorph is polymorphic Form I, and the X-ray powder diffraction pattern of the polymorphic Form I has characteristic peaks at 2θ values of 4.234±0.2°, 8.505±0.2°, 8.96±0.2°, 11.177±0.2°, 12.892±0.2°, 18.05±0.2°, 23.333±0.2°,

I

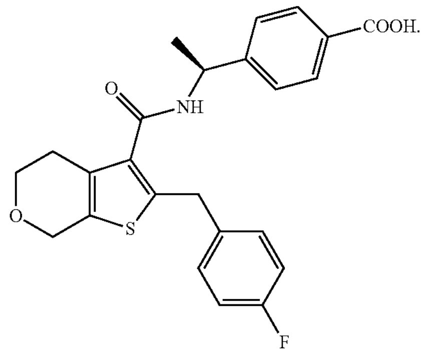

2. A pharmaceutical composition, wherein the pharmaceutical composition comprises:

(a) a polymorph of the compound of formula I according to claim 1, and (b) pharmaceutically acceptable carriers, wherein the pharmaceutical composition is in solid dosage form.

3. A method of treating a disease mediated by EP4 receptor activation, wherein the method comprises the step of: administering to a subject in need thereof a therapeutically effective amount of a polymorph of the compound of formula I according to claim 1 or pharmaceutical composition thereof, wherein the pharmaceutical composition is in solid dosage form, wherein the disease mediated by EP4 receptor activation is selected from the group consisting of: liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, cervical cancer, allergies, bone diseases, acute or chronic pain, or a combination thereof.

4. A preparation method of the polymorph according to claim 1, comprising the steps of: providing a mixed solution of the compound of formula I in a first solvent, slurrying, and filtering, so as to obtain the polymorphic Form I, or providing a mixed solution of the compound of formula I in a first solvent, stirring and filtering, so as to obtain the polymorphic Form I; or providing a mixed solution of the compound of formula I in a first solvent, and volatilizing, so as to obtain the polymorphic Form I;

wherein, the first solvent is selected from the group consisting of methanol, isopropanol, isobutanol, 2-butanone, acetonitrile, methyl tert-butyl ether, water, ethyl acrylate, acetone, isopropyl acetate, dichloromethane, n-heptane, 1,4-dioxane, butyl acetate, 4-methyl-2-pentanone, toluene, 2-butanone, cyclohexane, a mixed solution of THF and water, or a combination thereof.

5. A polymorph of a compound of formula I, wherein the polymorph is polymorphic Form II, and the X-ray powder diffraction pattern of the polymorphic Form II has characteristic peaks at 20 values of 4.018±0.2°, 8.722±0.2°, 9.382±0.2°, 11.539±0.2°, 17.732±0.2°, 18.038±0.2°, 19.13±0.2°,

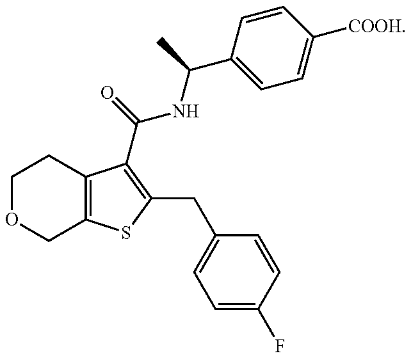

I

6. A pharmaceutical composition, wherein the pharmaceutical composition comprises:

(a) a polymorph of the compound of formula I according to claim 5; and (b) pharmaceutically acceptable carriers;

wherein the pharmaceutical composition is in solid dosage form.

7. A method of treating a disease mediated by EP4 receptor activation, wherein the method comprises the step of: administering to a subject in need thereof a therapeutically effective amount of a polymorph of the compound of formula I according to claim 5 or a pharmaceutical composition thereof, wherein the pharmaceutical composition is in solid dosage form, wherein the disease mediated by EP4 receptor activation is selected from the group consisting of: liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, cervical cancer, allergies, bone diseases, acute or chronic pain, or a combination thereof.

8. A preparation method of the polymorph according to claim 5, comprising the steps of:

providing a saturated solution of the compound of formula I in ethanol, undergoing cooling crystallization, and separating to obtain the polymorphic Form II; or providing a suspension of the compound of formula I in ethanol, stirring the suspension at 4-40° C. and separating to obtain the polymorphic Form II.

9. A polymorph of a compound of formula I, wherein the polymorph is polymorphic Form IV, and the X-ray powder diffraction pattern of the polymorphic Form IV has characteristic peaks at 20 values of 8.529±0.2°, 9.177±0.2°, 9.696±0.2°, 11.324±0.2°, 17.556±0.2°, 17.824±0.2°, 28.107±0.2°,

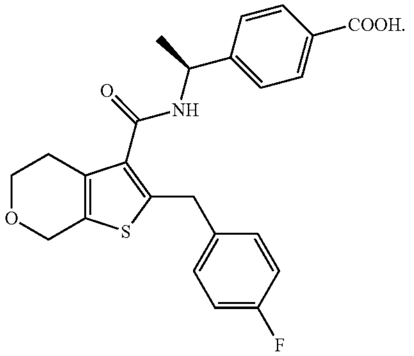

I

10. A pharmaceutical composition, wherein the pharmaceutical composition comprises:

(a) a polymorph of the compound of formula I according to claim 9; and (b) pharmaceutically acceptable carriers;

wherein the pharmaceutical composition is in solid dosage form.

11. A method of treating a disease mediated by EP4 receptor activation, wherein the method comprises the step of: administering to a subject in need thereof a therapeutically effective amount of a polymorph of the compound of formula I according to claim 9 or a pharmaceutical composition thereof, wherein the pharmaceutical composition is in solid dosage form, wherein the disease mediated by EP4 receptor activation is selected from the group consisting of: liver cancer, lung cancer, prostate cancer, skin cancer, colon cancer, pancreatic cancer, breast cancer, leukemia, lymphoma, ovarian cancer, gastric cancer, bladder cancer, kidney cancer, oral cancer, melanoma, esophageal cancer, cervical cancer, allergies, bone diseases, acute or chronic pain, or a combination thereof.

12. A preparation method of the polymorph according to claim 9, comprising the steps of:

providing a mixed solution of the compound of formula I in methanol, adding water to the mixed solution and volatilizing in a room temperature environment to obtain the polymorphic Form IV.

* * * * *